United States Patent [19]
Gorman et al.

[11] Patent Number: 5,830,878
[45] Date of Patent: Nov. 3, 1998

[54] CATIONIC LIPID: DNA COMPLEXES FOR GENE TARGETING

[75] Inventors: Cori M. Gorman; Molly McClarrinon, both of San Francisco, Calif.

[73] Assignee: Megabios Corporation, Burlingame, Calif.

[21] Appl. No.: 485,005

[22] Filed: Jun. 7, 1995

[51] Int. Cl.$^6$ ............................ A61K 48/00; C12N 15/64; C12N 15/85; C12N 15/88

[52] U.S. Cl. .......................... 514/44; 435/69.1; 435/91.1; 435/172.1; 435/172.3; 435/320.1; 435/375; 435/70.1; 435/6; 424/450

[58] Field of Search ............................... 514/44; 424/450; 435/172.3, 6, 69.1, 70.1, 91.4, 134, 240.2, 320.1, 375; 548/347.1

[56] References Cited

FOREIGN PATENT DOCUMENTS

| | | | |
|---|---|---|---|
| WO9314778 | 8/1993 | WIPO | A61K 37/00 |
| WO9426915 | 11/1994 | WIPO | C12N 15/86 |
| WO9514380 | 6/1995 | WIPO | A01N 25/26 |
| WO9514381 | 6/1995 | WIPO | A01N 25/26 |
| WO9514651 | 6/1995 | WIPO | C07C 69/52 |

OTHER PUBLICATIONS

Abstracts for WO 94 14380 PCT, Publ. Jun. 1, 1995 (a) Caplus Abstract AN 1995: 801602. (b) Derwent WPI Abstract AN 95–215055 [28] WPIDS.

I. Solodin et al Biochemistry 34: 13537–44 ('95).

Rahman et al., 1982, "Differential Uptake of Liposomes Varying in Size and Lipid Composition by Parenchymal and Kupffer Cells of Mouse Liver," *Life Sci.* 31:2061–2071.

Sambrook et al., 1990, *Molecular Cloning: A Laboratory Manual* (Cold Spring Harbor Press: New York).

Thomas & Capecchi, 1987, "Site–Directed Mutagenesis by Gene Targeting in Mouse Embryo–Derived Stem Cells," *Cell* 51:503–512.

Bertling, 1987, "Transfection of a DNA/Protein Complex into Nuclei of Mammalian Cells Using Polyoma Capsids and Electroporation," *Bioscience Reports* 7:107–112.

Smithies et al., 1985, "Insertion of DNA sequences into the human chromosomal β=globin locus by homologous recombination," *Nature* 317:230–234.

Innis et al., 1990, *PCR Protocols: A Guide to Methods and Applications*, Academic Press, New York.

Solodin et al., 1995, "A novel series of amphiphilic imidazolinium compounds for in–vitro and in–vivo gene delivery," *Biochemistry* 34, No. 41, 17 Oct. 1995.

Poste et al., 1974, "Lipid vesicles as carriers for introducing biological active materials into cells," *Methods Cell. Biol.* 14:33–71.

*Primary Examiner*—Charles C. P. Rories
*Attorney, Agent, or Firm*—McDonnell, Boehnen Hulbert & Berghoff

[57] ABSTRACT

This invention herein describes pharmaceutical compositions and methods for targeted delivery of functional genes into cells and tissues in vivo. The invention discloses DNA:lipid complexes, methods of making such complexes and methods of using such complexes for facilitating the targeted delivery and entry of recombinant expression constructs into cells and tissues in vivo, and particularly delivery of such recombinant expression constructs by intravenous, intraperitoneal or direct injection.

9 Claims, 10 Drawing Sheets

FIG. I
MEGABIOS FORMULATIONS ARE STABLE
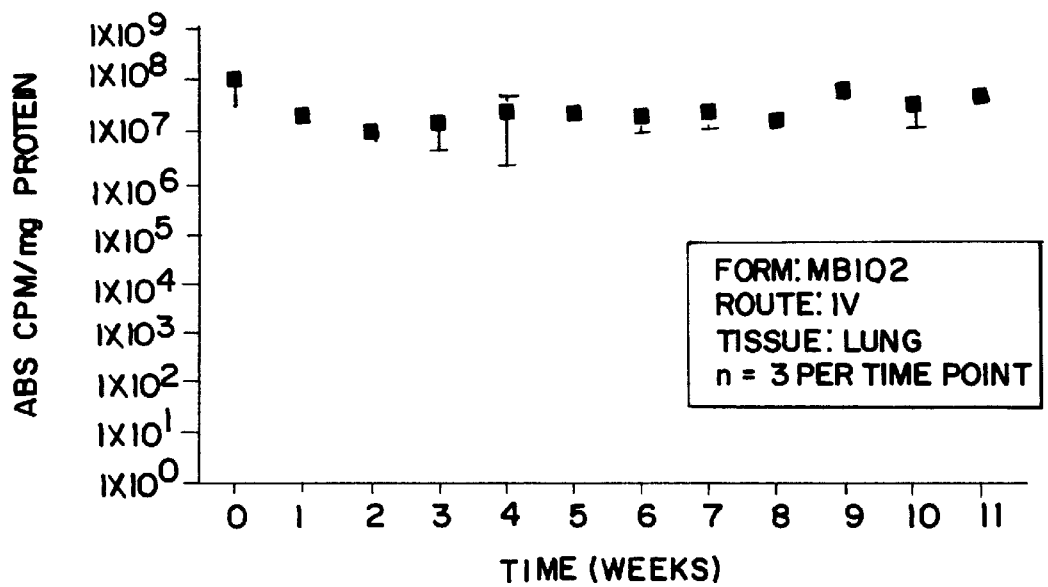
FIG. 2
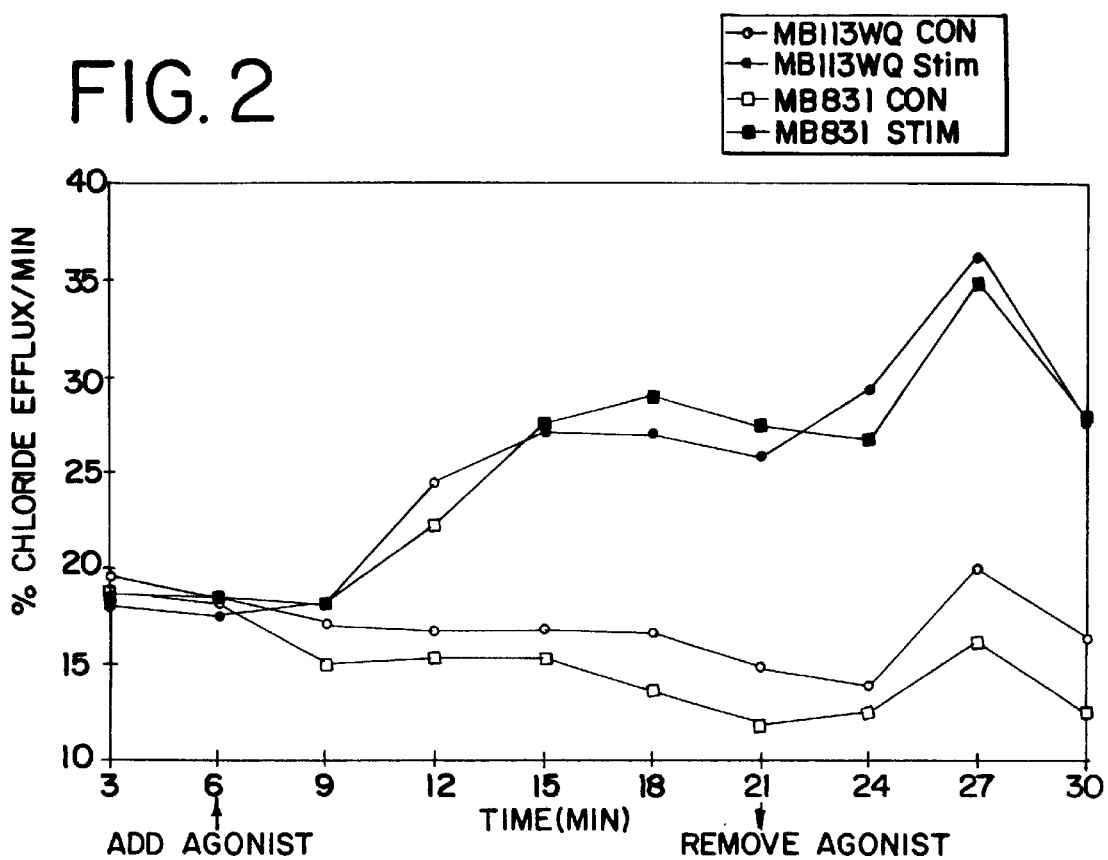

REPRODUCIBLE EXPRESSION

EXPRESSION VECTOR

HIGH, PERSISTENT EXPRESSION IN THE LUNG

SINGLE IV INJECTION IN MICE, FOLLOWED FOR 55 DAYS

FORMULATION DESIGN CAN SELECTIVELY TARGET THE LUNG OR SPLEEN

CHANGES IN FORMULATION CAN TARGET THE PANCREAS

EFFECT OF ROUTE OF ADMINISTRATION ON EXPRESSION

CATIONIC LIPID: DNA COMPLEXES FOR GENE TARGETING

BACKGROUND OF THE INVENTION

1. Field of the Invention

A perennial goal in the pharmacological arts has been the development of methods and compositions to facilitate the specific delivery of therapeutic and other agents to the appropriate cells and tissues that would benefit from such treatment, and the avoidance of the general physiological effects of the inappropriate delivery of such agents to other cells or tissues of the body. Recently, the advent of recombinant DNA technology and genetic engineering has provided the pharmacological arts with a wide new spectrum of agents that are functional genes carried in recombinant expression constructs capable of mediating expression of these genes in host cells. These developments have carried the promise of "molecular medicine", specifically gene therapy, whereby a defective gene could be replaced by an exogenous copy of its cognate, functional gene, thereby alleviating a variety of genetic diseases.

However, the greatest drawback to the achievement of effective gene therapy has been the inability in the art to introduce recombinant expression constructs encoding functional eukaryotic genes into cells and tissues in vivo. While it has been recognized in the art as being desirable to increase the efficiency and specificity of administration of gene therapy agents to the cells of the relevant tissues, the goal of specific delivery has not been achieved in the prior art.

Liposomes have been used to attempt cell targeting. Rahman et al., 1982, Life Sci. 31: 2061–71 found that liposomes which contained galactolipid as part of the lipid appeared to have a higher affinity for parenchymal cells than liposomes which lacked galactolipid. To date, however, efficient or specific delivery has not been predictably achieved using drug-encapsulated liposomes. There remains a need for the development of a cell- or tissue-targeting delivery system.

Thus there remains in the art a need for methods and reagents for achieving cell and tissue-specific targeting of gene therapy agents, particularly recombinant expression constructs encoding functional genes, in vivo.

BRIEF SUMMARY OF THE INVENTION

The present invention is directed to an improved methods for targeted delivery of functional eukaryotic genes to cells and tissues in vivo. This delivery system achieves such specific delivery by the formation of DNA:lipid complexes between nucleic acid comprising a recombinant expression construct encoding a functional eukaryotic gene or fragment thereof complexed with a mixture of a cationic lipid and a neutral lipid. Methods of use are also provided. This invention has the specific advantage of targeted delivery of functional eukaryotic genes into cells in vivo, achieving effective intracellular delivery of constructs encoding functional genes more efficiently and with more specificity than conventional delivery systems.

In a first embodiment, the invention provides a pharmaceutical composition, comprising a formulation of a soluble complex of a recombinant expression construct and a mixture of a neutral lipid and a cationic lipid in a pharmaceutically acceptable carrier suitable for administration to an animal by injection. In these embodiments of the invention, the recombinant expression construct comprises a nucleic acid encoding a protein, the nucleic acid being operatively linked to gene expression regulatory elements and whereby the protein encoded by the nucleic acid is expressed.

In this first embodiment, the cationic lipid is a nitrogen-containing, imidazolinium-derived cationic lipid having the formula:

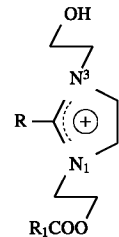

wherein each of R and $R_1$ independently is a straight-chain, aliphatic hydrocarbyl group of 11 to 29 carbon atoms inclusive. Preferred are those cations wherein each of R and $R_1$ independently have from 13 to 23 carbon atoms inclusive. In particularly preferred embodiments, the cationic lipid is 1-(2-(oleoyloxy)ethyl)-2-oleyl-3-(2-hydroxyethyl)imidazolinium. In additional preferred embodiments, the neutral lipid is cholesterol, and the 1-(2-(oleoyloxy)ethyl)-2-oleyl-3-(2-hydroxyethyl)imidazolinium and cholesterol are present in the complex at a ratio of 1:1. Further preferred embodiments comprise a recombinant expression construct encoding human CFTR and a mixture of a neutral lipid and a cationic lipid comprises a ratio of DNA to lipid of from about 1:6 to about 1:8 ($\mu$gDNA:nmoles lipid). Particularly preferred are embodiments where the DNA comprising the recombinant expression construct is present in the complex at a concentration of about 0.5 to 1 mg/mL. In further preferred embodiments, the cationic lipid is 1-(2-(oleoyloxy)ethyl)-2-oleyl-3-(2-hydroxyethyl)imidazolinium and the neutral lipid is dioleoylphosphatidylethanolamine, and the 1-(2-(oleoyloxy)ethyl)-2-oleyl-3-(2-hydroxyethyl) imidazolinium and dioleoylphosphatidylethanolamine are present in the complex at a ratio of 1:1. Further preferred embodiments comprise a recombinant expression construct and a mixture of a neutral lipid and a cationic lipid comprises a ratio of DNA to lipid of about 1:1. Particularly preferred are embodiments where the DNA comprising the recombinant expression construct is present in the complex at a concentration of about 0.5 to 5 mg/mL.

In a second embodiment, the invention provides methods for introducing a recombinant expression construct into a cell comprising lung tissue in an animal, the method comprising the step of administering the pharmaceutical composition of claim 1 to the animal by intravenous injection. In preferred embodiments, the cationic lipid is 1-(2-(oleoyloxy)ethyl)-2-oleyl-3-(2-hydroxyethyl) imidazolinium. In additional preferred embodiments, the neutral lipid is cholesterol, and the 1-(2-(oleoyloxy)ethyl)-2-oleyl-3-(2-hydroxyethyl)imidazolinium and cholesterol are present in the complex at a ratio of 1:1. Further preferred embodiments comprise a recombinant expression construct and a mixture of a neutral lipid and a cationic lipid comprises a ratio of DNA to lipid of from about 1:6 to about 1:8. Particularly preferred are embodiments where the DNA comprising the recombinant expression construct is present in the complex at a concentration of about 0.5–1 mg/mL.

In another aspect of the second embodiment of the invention is provided methods for introducing a recombinant expression construct into a cell comprising spleen tissue in an animal, the method comprising the step of administering the pharmaceutical composition of claim 1 to the animal by intravenous injection. In preferred embodiments, the cationic lipid is 1-(2-(oleoyloxy)ethyl)-2-oleyl-3-(2-hydroxyethyl)imidazolinium. In additional preferred embodiments, the neutral lipid is dioleoylphosphatidylethanolamine, and the cationic lipid and the neutral lipid are present in a ratio of 1:1. Further preferred embodiments comprise a recombinant expression construct and a mixture of a neutral lipid and a cationic lipid comprises a ratio of DNA to lipid of about 1:1. Particularly preferred are embodiments where the DNA comprising the recombinant expression construct is present in the complex at a concentration of about 1–2.5 mg/mL.

In further embodiments, the DNA:lipid complex is targeted to peritoneal macrophages by administration by intraperitoneal injection. In these embodiments, the cationic lipid is 1-(2-(oleoyloxy)ethyl)-2-oleyl-3-(2-hydroxyethyl) imidazolinium, the neutral lipid is cholesterol, the cationic lipid and the neutral lipid are present in a ratio of about 1:1, the complex of a recombinant expression construct and a mixture of a neutral lipid and a cationic lipid comprises a ratio of DNA to lipid of about 1:1, the DNA concentration in the DNA:lipid complexes is about 1–2.5 mg/mL. In additional embodiments of this aspect of the invention, the DNA:lipid complex is targeted to spleen macrophages and administered by intraperitoneal injection. In these embodiments, the cationic lipid is 1-(2-(oleoyloxy)ethyl)-2-oleyl-3-(2-hydroxyethyl)imidazolinium, the neutral lipid is cholesterol, the cationic lipid and the neutral lipid are present in a ratio of about 1:1, the complex of a recombinant expression construct and a mixture of a neutral lipid and a cationic lipid comprises a ratio of DNA to lipid of about 1:1, the DNA concentration in the DNA:lipid complexes is about 1 to 2.5 mg/mL.

In this aspect, the invention also provides methods for targeting gene transfer into pancreatic tissue by intraperitoneal injection. In preferred embodiments, the cationic lipid is 1-(2-(oleoyloxy)ethyl)-2-oleyl-3-(2-hydroxyethyl) imidazolinium, the neutral lipid is dioleoylphosphatidylethanolamine, the cationic lipid and the neutral lipid are present in a ratio of about 1:1, the complex of a recombinant expression construct and a mixture of a neutral lipid and a cationic lipid comprises a ratio of DNA to lipid of about 1:1, the DNA concentration in the DNA:lipid complexes is about 1.5 to about 2.5 mg/mL.

The invention also provides a method of introducing a recombinant expression construct into a cell comprising a tissue in an animal, the method comprising the step of administering the pharmaceutical composition of claim 1 to the animal by direct injection. In preferred embodiments, the cationic lipid is 1-(2-(oleoyloxy)ethyl)-2-oleyl-3-(2-hydroxyethyl)imidazolinium and the neutral lipid is cholesterol. Also preferred are mixtures of the cationic lipid and the neutral lipid in a ratio of about 1:1. Preferred complexes include a complex of a recombinant expression construct and a mixture of a neutral lipid and a cationic lipid comprising a ratio of DNA to lipid of about 1:1. The preferred DNA concentration in the DNA:lipid complexes is about 1–2.5 mg/mL in this embodiment of the invention.

Specific preferred embodiments of the present invention will become evident from the following more detailed description of certain preferred embodiments and the claims.

BRIEF DESCRIPTION OF THE DRAWINGS

FIG. 1 is a graph showing the stability of DNA:liposome complexes of the invention assayed by intravenous administration and lung CAT assays over a period of 11 weeks.

FIG. 2 is a graph of a comparison of chloride efflux in the presence and absence of stimuli in cells transfected with human CFTR-encoding plasmid vectors complexed with EDMPC:cholesterol.

DETAILED DESCRIPTION OF THE PREFERRED EMBODIMENTS

Figure 3:
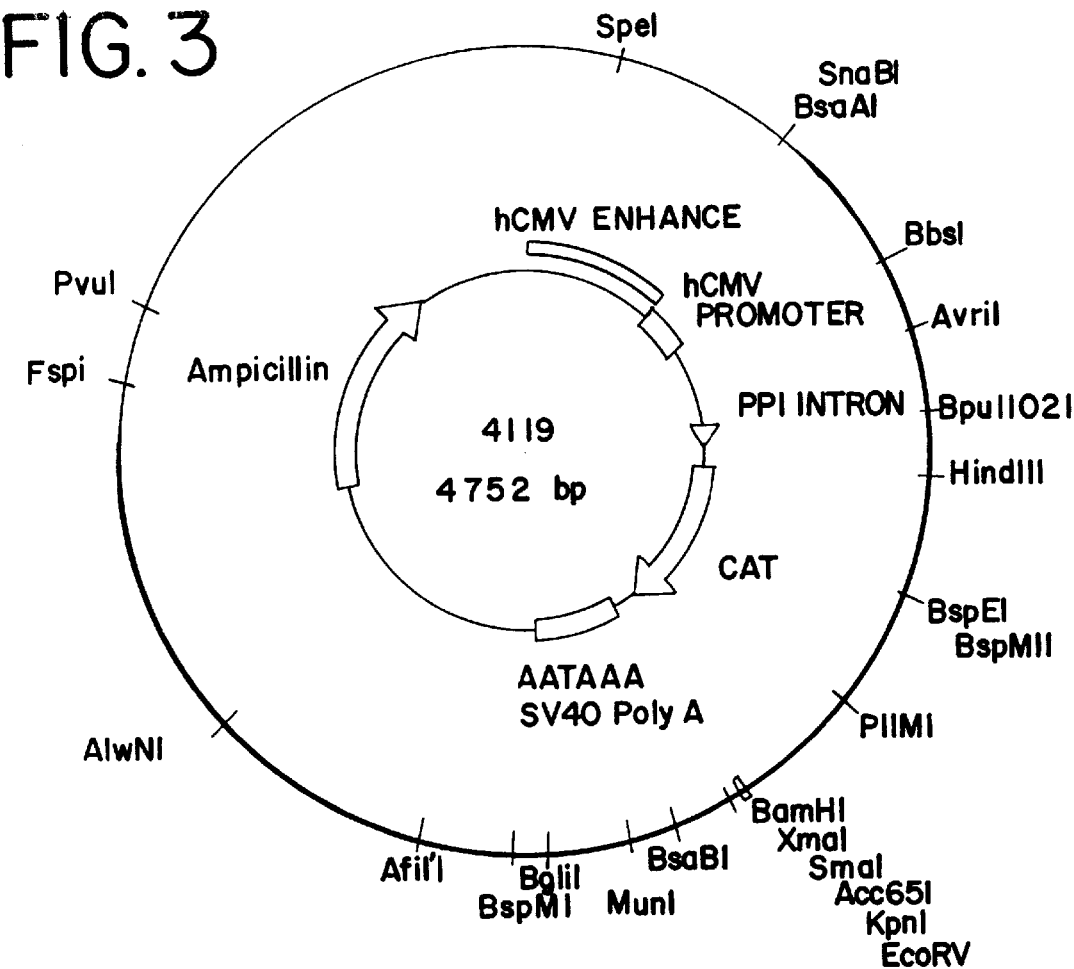
FIG. 3 is a schematic representation of the plasmid p4119.

The present invention provides compositions of matter and methods for facilitating the entry into cells of nucleic acids, particularly recombinant expression constructs encoding functional eukaryotic genes. For the purposes of this invention, the term "recombinant expression construct" is intended to encompass a replicable DNA construct comprising a nucleic acid encoding a functional gene or fragment thereof, operably linked to suitable control sequences capable of effecting the expression of the gene in a suitable host cell. Expressly intended to fall within the definition of a "gene" are embodiments comprising cDNA and genomic DNA embodiments of functional eukaryotic genes, as well as chimeric hybrids thereof. Also intended to fall within the scope of the recombinant expression constructs of the invention are fragments of such genes which, when expressed, may inhibit or suppress the function of an endogenous gene in a cell, including, inter alia, antisense gene fragments or ribozymes.

In the recombinant expression constructs as provided by the present invention, the need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratible DNA fragments (i.e., fragments integratable into the host genome by homologous or non-homologous recombination). Also useful are vectors which replicate autonomously in host cells. Suitable vectors will contain replicon and control sequences which are derived from species compatible with the intended expression host cell.

The recombinant expression constructs of the present invention are useful in gene therapy, and specifically, delivering exogenous copies of a defective gene to a specific tissue target in vivo. See generally Thomas & Capecchi, 1987, Cell 51: 503–512; Bertling, 1987, Bioscience Reports 7: 107–112; Smithies et al., 1985, Nature 317:230–234.

The invention provides complexes of recombinant DNA constructs encoding functional eukaryotic genes or fragments thereof and also comprising a mixture of a cationic lipid and a neutral lipid. For the purposes of this invention, the term "cationic lipid" is intended to encompass lipids which are positively charged at physiological pH, and more particularly, constitutively positively charged lipids comprising, for example, a quaternary ammonium salt moiety. Expressly within the teachings of the present invention are co-owned and co-pending U.S. patent applications, Ser. Nos. 08/245,737, filed May 18, 1994; 08/248,005, filed May 24, 1994; 08/247,963, filed May 24, 1994; 08/157,637, filed Jun. 7, 1994; and International Patent Application Nos. PCT/US94/13428, filed Nov. 17, 1994; PCT/US94/13363, filed Nov. 17, 1994; and PCT/US94/13362, filed Nov. 17, 1994, which are all herein incorporated by reference in their entireties.

Specifically, the invention provides nitrogen-containing, imidazolinium derived cationic lipids having the formula:

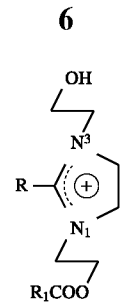

wherein each of R and $R_1$ independently is a straight-chain, aliphatic hydrocarbyl group of 11 to 29 carbon atoms inclusive. Preferred are those cations wherein each of R and $R_1$ independently have from 13 to 23 carbon atoms inclusive. The R and $R_1$ groups are saturated or are unsaturated having one or more ethylenically unsaturated linkages and are suitably the same or are different from each other. Illustrative $R_1$ groups include lauroyl, myristoyl, palmitoyl, stearoyl, linoleoyl, eicosanoyl, tricosanoyl and nonacosanoyl. In preferred embodiments, the cationic lipid is 1-(2-(oleoyloxy)ethyl)-2-oleyl-3-(2-hydroxyethyl) imidazolinium (abbreviated as DOTIM herein).

The cationic lipids comprising the liposome formulations of the invention can be synthesized by a rearrangement reaction disclosed in co-owned and co-pending U.S. Ser. No. 08/247,963, filed May 24, 1994, incorporated by reference herein. This reaction comprises synthesis of DOTIM from N,N-bis(2-hydroxyethyl)ethylenediamine through an amino-protected diacylated intermediate to the desired product. The method in general involves synthesis of an imidazolinium ion by heating a precursor compound of formula

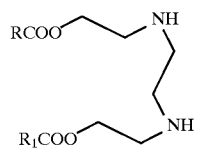

in an organic solvent at a temperature above the boiling point of water, wherein each of R and $R_1$ independently represents an organic group such that the precursor compound is soluble in the solvent and the R and $R_1$ are stable against reaction in the solvent at the temperature. The general synthetic method (including some non-essential steps directed to preferred embodiments and preliminary reactions prior to the key step) can be found in U.S. Ser. No. 08/247,963; this cationic lipid is also commercially available (Avanti Polar Lipids, Ala.).

Cationic lipids are particularly useful as carriers for anionic compounds, particularly polyanionic macromolecules such as nucleic acids. As cationic lipids are positively charged, a tight charge complex can be formed between a cationic lipid carrier and a polyanionic nucleic acid, resulting in a lipid carrier-nucleic acid complex which can be used directly for systemic delivery to a mammal or mammalian cell.

Neutral lipids are characterized in contrast to the cationic lipids of the invention and are characterized as being electrochemically neutral, although this definition does not preclude protonation of such lipids to produce a positively-charged salt under certain conditions. Expressly included within this definition are, inter alia, cholesterol and dioleoylphosphatidyl ethanolamine.

Complexes of DNA and mixtures of cationic and neutral lipids of the invention are characterized by a number of parameters intrinsic to the formation of such complexes. These include the identity of the cationic lipid and the neutral lipid; the ratio of cationic lipid to neutral lipid; concentration of DNA in the complex; the ratio of DNA to lipid; DNA purity; cationic liposome size; methods of preparing liposomes; the methods of preparing the DNA:liposome complexes; and other variables. Preferred combinations of cationic and neutral lipids include 1-(2-(oleoyloxy) ethyl)-2-oleyl-3-(2-hydroxyethyl)imidazolinium and cholesterol and 1-(2-(oleoyloxy)ethyl)-2-oleyl-3-(2-hydroxyethyl)imidazolinium and dioleoylphosphatidyl ethanolamine. A preferred ratio of these lipids is 1:1. DNA concentration in the complexes is from about 0.5 mg/mL to about 5 mg/mL, more preferably from about 0.5 mg/mL to about 2.5 mg/mL. DNA:lipid ratios are preferably from about 1:1 for formulations to be injected intraperitoneally, to from about 1:6 to 1:8 for preparations to be injected intravenously. DNA purity has a direct effect on liposome complex formation, but DNAs having a purity of about 15% to about 90% are appropriate for complex formation.

The various lipid carrier-nucleic acid complexes wherein the lipid carrier is a liposome are prepared using methods well known in the art. Mixing conditions can be optimized by visual examination of the resultant lipid-DNA mixture to establish that no precipitation occurs. To make the lipid-DNA complexes more visible, the complexes that can be stained with a dye which does not itself cause aggregation, but which will stain either the DNA or the lipid. For example, Sudan black (which stains lipid) can be used as an aid to examine the lipid-DNA mixture to determine if aggregation has occurred. Particle size also can be studied with methods known in the art, including electronic microscopy, laser light scattering, Coulter™ counting/sizing, and the like. Standard-size beads can be included as markers for determining the size of any liposomes or aggregates that form. By "lipid carrier-nucleic acid complex" is meant a nucleic acid sequence as described above, generally bound to the surface of a lipid carrier preparation, as discussed below. The lipid carrier preparation can also include other substances or cofactors. Furthermore, the lipid carrier-nucleic acid complex can include targeting agents to deliver the complex to particular cell or tissue types. Generally, the nucleic acid material is added to a suspension of preformed liposomes which may be multi-lamellar vesicles (MLVs) or small unilamellar vesicles (SUVs), usually SUVs formed by sonication. The liposomes themselves are prepared from a dried lipid film that is resuspended in an appropriate mixing solution such as sterile water or an isotonic buffer solution such as 10 mM Tris/NaCl or 5% dextrose in sterile water and sonicated to form the liposomes. Then the preformed lipid carriers are mixed directly with the DNA.

Mixing and preparing of the lipid-DNA complex can be critically affected by the sequence in which the lipid and DNA are combined. Generally, it is preferable (to minimize aggregation) to add the lipid to the DNA at ratios of DNA:lipid of up to 1:2 inclusive (microgram DNA:nanomoles cationic lipid). Where the ratio of DNA:lipid is 1:4 or higher, better results are generally obtained by adding the DNA to the lipid. In either case, mixing should be rapidly achieved by shaking or vortexing for small volumes and by use of rapid mixing systems for large volumes. The lipid carrier and DNA form a very stable complex due to binding of the negatively charged DNA to the cationic lipid carriers. SUVs find use with small nucleic acid fragments as well as with large regions of DNA ($\geq 30$ kb).

Aggregation of the lipid carrier-nucleic acid complex is prevented by controlling the ratio of DNA to lipid carrier, minimizing the overall concentration of DNA:lipid carrier complex in solution, usually less than 5 mg DNA/mL solution, and avoiding the use of chelating agents such as EDTA and/or significant amounts of salt, either of which tends to promote macro-aggregation. The preferred excipient is water, dextrose/water or another solution having low or zero ionic strength. Further, the volume should be adjusted to the minimum necessary for injection into the host mammal, while at the same time taking care not to make the solution too concentrated so that aggregates form.

Liposomes of the invention may be sized in accordance with conventional techniques, depending upon the desired size.

The DNA:lipid complexes of the invention have utility in mediating the efficient delivery of the recombinant expression constructs of the invention, encoding functional eukaryotic genes of fragments thereof, into eukaryotic, preferably mammalian, most preferably human cells. DNA:lipid complexes of the invention are useful for achieving gene transfer in vitro using established techniques. More importantly, the DNA:lipid complexed provided by this invention, and the methods of administering the DNA:lipid complexes provided herein, are capable of specifically delivering recombinant expression constructs of the invention to particular tissues and cells comprising those tissues in vivo, thereby providing targeting of these genes to specific tissues. These properties of the pharmaceutical compositions and methods of the present invention provide for real gene therapy, whereby a particular deficient gene is restored by the introduction of a functional copy of the normal cognate gene into the cells of the affected tissue, without deleterious and unpredictable results from inappropriate introduction of the construct into other cells and tissues of the body nonspecifically.

Thus, the invention provides methods and pharmaceutical compositions having a number of advantages over the prior art. The liposomes and lipid complexes of the invention have been extensively studied in humans, and are non-immunogenic, relatively non-toxic, and non-infectious. These complexes are stable, as illustrated by the experimental results shown in FIG. 1. A particular DNA:liposome complex (DOTIM:Cholesterol (1:1) complexed with a CAT-encoding plasmid at a DNA: lipid ratio of 1:6 and a DNA concentration of 0.625 mg/mL) was prepared and tested weekly over 11 weeks by injection into the tail vein of ICR mice. CAT activity was then determined in mouse lung using protocols described in detail below. The Figure shows results demonstrating that this preparation was stable over the course of the experiment, whereby substantially identical levels of CAT gene expression were obtained at all time points tested.

The DNA:lipid complexes of the invention have additional advantages over the prior art. Recombinant expression constructs of any practicable size can be used, there being no limitation on large plasmid size due to the absence of packaging the DNA into the genome of a vector organisms like a retrovirus or an adenovirus. Gene transfer can be achieved in non-dividing cells, unlike prior art systems which relied on viral vectors whose life cycle required the infected cells to be dividing. In addition, the specific formulation of the DNA:lipid complexes of the invention can be altered to affect targeting and duration of the gene-expression effect. The DNA:lipid complexes of the invention are also amenable to many delivery routes, and are less likely to encounter the types of severe regulatory requirements anticipated for viral-based delivery systems.

The DNA:lipid complexes of the invention may be administered to an animal to effect delivery of functional genes into specific tissues by any appropriate therapeutic routine, including intravenous, intraperitoneal, subcutaneous, or intramuscular injection; direct injection into the target tissue(s). Typically, the DNA:lipid complexes of the invention are injected in solution where the concentration of the DNA to be delivered dictates the amount of the complex to be administered. This amount will vary with the tissue to be targeted and the effectiveness of the targeted DNA, the required concentration for the desired effect, the number of administrations, and the like.

The methods and pharmaceutical compositions of the invention thus are particularly useful and appropriate for introducing functional human genes, particularly human CFTR, to lung tissue. These methods and pharmaceutical compositions thus have utility in the treatment of human diseases, including cystic fibrosis and chronic bronchitis.

The following Examples illustrate certain aspects of the above-described method and advantageous results. The following examples are shown by way of illustration and not by way of limitation.

EXAMPLE 1

Preparation of DOTIM:Cholesterol (1:1) Small Unilamellar Vesicles

To a 1L round bottom flask was added 500 µmoles cholesterol dissolved in an excess of chloroform and then 500 µmoles DOTIM also dissolved in an excess of chloroform. The amount of DOTIM was determined by phosphorus assay and not simply on the basis of the dry weight of the reagent.

After brief, gently mixing, the flask was attached to a rotary evaporating apparatus and chloroform withdrawn under slow speed and water vacuum conditions until almost all of the solvent was evaporated. Evaporation was completed at maximum rotation speed using a vacuum pump to completely dry the lipid mixture to a thin film on the wall of the round bottom flask.

As an intermediate step to the formation of the title composition, multilamellar vesicles (MLVs) were prepared from this film by the addition of 16 mL endotoxin-free water to the flask, which was then warmed to 37° C. in a water bath with gentle hand-swirling. The MLVs thus formed were removed from the flask using a 9" Pasteur pipette and transferred to a 20 mm screw cap tube at room temperature. The flask was cleared of any remaining MLVs by washing with an additional 4 mL endotoxin-free water, which was added to the 16 mL previously transferred from the flask. These solutions were mixed, and aliquotted equally into 20 16 mL screw cap tubes using a Pasteur pipette.

MLVs were converted into the SUVs of the title composition by sonication. Each of the 16 mL screw cap tubes containing MLVs were placed individually into a sonicating water bath maintained at 36° C. for 5 min, and the temperature of the bath checked between the introduction of each tube. Sonicated droplets within each tube were collected by brief vortex mixing, and the individual solutions of SUVs were then combined into a single 20 mm screw cap tube using a 9" Pasteur pipette, and then filtered using a 0.2 micron disposable filter (Nalgene). Finally, an amount of an endotoxin-free solution of 25% dextrose in water, equal to one-quarter of the final volume of SUVs, was added to the tube of SUVs. This resulted in a suspension of SUVs comprising 20 mM DOTIM and 20 mM cholesterol (40 mM total lipid) in a 5% dextrose solution, which was kept at 4° C. until use.

EXAMPLE 2

Large Scale Plasmid DNA Preparation

Plasmid DNA was prepared in large-scale (i.e., milligram) quantities using a modification of the alkaline lysis procedure (Sambrook et al., 1990, ibid.). Briefly, bacteria comprising a single colony were grown for 12–18 hours or overnight in 15 mL TB broth (47 g/L TB (Sigma Chemical Co., St. Louis, Mo.)/ 8% glycerol) supplemented with 100 µg/mL carbenicillin at 37° C. with shaking (250 rpm). 2–2.5 mL of this culture was then added to 40 mL TB (supplemented with 100 µg/mL carbenicillin) in each of six 2L flasks (for a total of 2.4L culture) and grown at 37° C. with shaking overnight (16–18 h).

After overnight growth, bacteria were collected by centrifugation for 10 min. at 4° C. in a Beckman J2-MI centrifuge equipped with a JA-10 rotor. The bacterial pellet in each centrifuge bottle was gently resuspended in 20 mL of an ice-cold solution of 50 mM dextrose in 25 mM HCl buffer (pH8)/10 mM EDTA. To the resuspended bacterial cell pellets were added 40 mL of a freshly-made solution of 0.2N NaOH/1% sodium dodecyl sulfate at room temperature, resulting in cell lysis upon gentle agitation of this mixture on ice for about 5 min. After the added lysis solution has been thoroughly mixed into the bacterial suspension and the cells lysed, the mixture was allowed to stand at room temperature for 5 min. To this mixture of lysed bacteria was added 20 mL of an ice-cold solution of 3M potassium acetate, which was mixed into the lysed bacterial solution gently by hand and then stored on ice for 10 min. A flocculent white precipitate formed, comprising bacterial chromosomal DNA, RNA and SDS/protein/membrane complexes, which were cleared from the solution by centrifugation at 8000 rpm for 15 min at 4° C. in the JA-10 rotor as above.

After centrifugation, the supernatant was transferred with filtering through Miracloth to 250 mL centrifuge bottles, and 50 mL isopropanol added at room temperature, mixed and incubated for 10 min. The plasmid DNA precipitate was recovered by centrifugation at 5000 rpm for 10 min at room temperature in a JA-14 rotor (Beckman). The alcohol-containing supernatant was decanted and residual supernatant removed by vacuum aspiration.

The plasmid DNA pellets were resuspended in 6 mL of a solution of 6 mM Tris-HCl (pH8) and transferred to 50 mL centrifuge tubes upon dissolution. To each tube was added and equal volume of cold (−20° C.) 5M LiCl, the solutions mixed by hand and then centrifuged at 8000 rpm for 10 min at room temperature in a JA-20 rotor (Beckman). The supernatant solution from each tube was transferred to a fresh tube and the plasmid DNA then re-precipitated by the addition of an equal volume of isopropanol, mixed and collected by centrifugation at 5000 rpm for 10 min at room temperature in a JA-20 rotor. The alcohol-containing supernatant solution was then decanted, residual alcohol removed by aspiration, and the plasmid DNA pellets allowed to air dry for 5 min.

Contaminating bacterial RNA was removed from the plasmid DNA by dissolving the pellets in 1 mL 10 mM Tris-HCl (pH8), adding about 0.5–0.75 kg of pancreatic RNase per mL, followed by incubating the mixture at 37° C. for 1 h. Disappearance of RNA was determined by ethidium bromide-stained agarose gel analysis (see Sambrook et al., ibid.).

Plasmid DNA was purified by phenol-chloroform extraction. Briefly, to each aliquot of plasmid DNA solution was added an equal volume of Tris-saturated phenol:chloroform (1:1), the immiscible solutions mixed by vortexing, and centrifuged in a laboratory tabletop microfuge for 5 min at room temperature. The aqueous (upper) layer was removed, transferred to a fresh microfuge tube, and extraction with phenol:chloroform repeated at least twice. These extractions were followed by two extractions of the aqueous layer with Tris-saturated chloroform. Plasmid DNA was concentrated by precipitation, with the addition of 5M sodium acetate to a final concentration of 0.3M and the addition of two volumes of cold (−20° C.) absolute ethanol. DNA was allowed to precipitate in this solution at −20° C. for 1 h or overnight.

After precipitation, plasmid DNA was collected by centrifugation at about 6000 rpm in a clinical microcentrifuge. The alcohol-containing supernatant was aspirated by vacuum, and the pellet washed twice with 70% ethanol/water (4° C.). The washed pellets were air dried for at least 30 min. Plasmid DNA pellets were dissolved in a total of 6 mL of a solution of 10 mM Tris-HCl (pH8), and concentration determined by spectrophotometric analysis of a 1-to-200 dilution of the recovered plasmid at $A_{260}$.

EXAMPLE 3

Preparation of DNA:Liposome Complexes

DOTIM:Cholesterol:Plasmid DNA liposomes were prepared as follows. A DOTIM:Cholesterol mixture (1:1, 20 μmoles/μL each lipid) was prepared as described in Example 1 above. Complexes with plasmid DNA were prepared in DNA:liposome ratios of 1:1 and 1:6. DNA and DOTIM:Cholesterol were each first brought from storage conditions (−20° C. for DNA, 4° C. for liposome formulations) to room temperature before use over the course of about 1.5 h. DNA concentration in the liposome preparations were optimally 100–550 μg/200 μL complex (for ratios of 1:1 DNA:liposomes) and 100–150 μg/μL complex (for ratios of 1:6 DNA:liposomes). DNA concentrations were typically determined just prior to DNA:liposome complex formation, by ultraviolet spectrophotometry as described in Example 2. DOTIM:Cholesterol mixtures were typically used at a total lipid concentration of 40 μmole/mL, corresponding to 20 μmole/mL DOTIM and 20 μmole/mL cholesterol.

DNA:liposome complexes were prepared from these reagents as follows. Each component was prepared in individual microfuge tubes to a total volume per tube of 100 μL. An appropriate amount of DNA (equivalent to a final DNA concentration of 500 μg DNA/mL complex) was added to one tube, and brought to volume with water or a solution of 5% dextrose in water. The appropriate amount of the DOTIM:Cholesterol mixture (100 nmoles lipid/100 μg DNA at a 1:1 ratio; 600 nmoles lipid/100 μg DNA at a 1:6 ratio) was added to a second tube, and water or a solution of 5% dextrose in water was added to bring this solution to a total volume of 100 μL. The contents of the lipid-containing tube were mixed by vortexing for about 2 sec, while the contents of the DNA-containing tube were mixed gently using a 1 mL pipettor. The contents of the lipid mixture-containing tube were then added to the DNA-containing tube using a 1 mL pipettor. It was found that it was essential that this addition was performed slowly, in a constant stream, to the top of the DNA solution in tube A. As the lipid solution mixed with the DNA, formation of the DNA:liposome complex was detected by the solution becoming slightly cloudy and opalescent. It was also determined that, at this stage, the mixture could not be vigorously mixed (for example, by vortexing) without seriously compromising the integrity and usefulness of the complexes so formed; however, it was advantageous to gently mix the entire contents of the tube 3–4 times after completion of addition of the lipid mixture to the DNA mixture.

After the complexes were formed, the final concentration of DNA was determined by ultraviolet spectrophotometry as described above, and the size of the DNA:liposome complexes determined by light scattering measured at 400 nm.

EXAMPLE 4

Preparation of Tissue Samples for CAT Assay and Protein Determination

Tissues were prepared for assay as follows. Experimental animals were euthanized quickly and humanely. Mice were typically placed in a kill box flooded with $CO_2$ for 2–3 min. Tissues were harvested by dissection and weighed, and then placed in 1 mL cold homogenation buffer (250 mM Tris/5 mM EDTA) supplemented with PMSF (35 μg/mL) and Leupeptin/Aprotinin (5 μg/mL). Tissues were then homogenized for 20–30 sec using a tissue disruptor (such as a Polytron) until a uniform homogenate was obtained. This homogenate was then transferred to a centrifuge tube and quickly frozen on dry ice (or at −70° C.) and then thawed at 37° C. Insoluble debris was cleared from the homogenate by centrifugation at 10,000 g for 5–10 min. 50 μL of the resulting supernatant solution was aliquotted into a microfuge tube and stored at −70° C. until used for protein determinations.

The remainder of the supernatant was heat inactivated at 65° C. for 15 min and recentrifuged at 10,000 g for 10 min, and stored at −70° C. until use for CAT assay determinations.

To perform CAT assays, samples were analyzed in parallel with a series of standard CAT activity samples. From the standards was developed a standard curve of CAT activity versus CAT protein, which was used to determine the level of CAT protein expression in tissue samples based on the observed CAT activity in tissue homogenates. To prepare the standard curve, serial dilutions of CAT enzyme were prepared ranging from 0.1 to 0.000025U. These standards were prepared in a reaction mixture consisting of 50 μL BSA buffer (250 mM Tris/5 mM EDTA/2 mg/mL BSA, Fraction V (U.S. Biochemical, Cleveland, Ohio), 5 μL standard CAT enzyme (and appropriate dilutions; obtained from Sigma Chemical Co, St. Louis, Mo.), 50 μL $^{14}$C-labeled chloramphenicol (New England Nuclear; diluted 1:10 in BSA buffer prior to use) and 25 μL n-butyryl-CoA (Sigma). Tissue samples were prepared identically, with the exception that 30 μL of tissue homogenate was substituted for the 5 μL of standard CAT enzyme activity. Samples were incubated at 37° C. for 2 h. After this incubation, 300 μL of mixed xylenes (Aldrich Chemical Co.) were added to each tube, vortexed for 30 sec, and centrifuged for 3 min at 10,000 rpm in an IEC centrifuge equipped with a 24-slot rotor. The mixed xylene (upper) phase of each sample tube was transferred to a fresh microfuge tube and 750 μL homogenation buffer added. The samples were then vortexed and centrifuged as described above.

200 μL of the upper phase from each tube were transferred to liquid scintillation vials and 0.5 mL scintillation cocktail (Ready-Safe, Beckman) added. The amount of CAT-specific radioactivity in each sample was determined by liquid scintillation counting assay.

EXAMPLE 5

X-Gal Staining of Tissue Samples

Tissue samples were stained with X-gal (5-bromo-4-chloro-3-indolyl-α-$_D$-galactopyranoside using the following protocol. Tissues are fixed by immersion for 0.5–1 h on ice in freshly-made fixative solution (2% neutral buffered formalin/0.02% gluteraldehyde/0.02% Nonidet-P40). After fixation, tissues were rinsed twice at 4° C. in a solution of 2 mM $MgCl_2$/0.1% desoxycholate/0.2% NP-40 in 10 mM phosphate-buffered saline (PBS; pH 7.3). Tissues were then stained using rinse solution supplemented with 1 mg/mL X-Gal (U.S. Biochemical), 5 mM ferricyanide and 5 mM ferrocyanide. Tissues were stained for 12–48 h at 37° C. or room temperature. After staining, tissues are rinsed in PBS. Tissues were then frozen and sectioned or fixed in 70% ethanol, embedded in paraffin and sectioned.

Protein determinations were performed using a dye binding assay (BCA PRotein Assay Reagent, Pierce Chemical Co.). The Pierce reagent was prepared by mixing 50 parts of Reagent A with 1 part Reagent B as provided by the supplier. 100 μL of this prepared reagent were aliquotted into each well of a 96 well microtiter plate. 100 μL of a solution containing 20 μg BSA were added to the first well of the first row (i.e., well A1) and 100 μL of a 1:2 to 1:8 dilution of each tissue extract were added to the other wells in the row. Serial dilutions at ratios of 1:2 were made in each of the adjoining rows consecutively using the wells in the preceding row. Typically, 96-well plates having 12 wells/row resulted in 6 serial dilutions (1 to 1/64); the last row is a blank loaded with PBS as a control. The plates were incubated at 37° C. for 30 minutes, and the extent of dye binding determined spectrophotometrically as absorbance at 562 nm. Protein concentrations in sample wells were determined in comparison with a standard curve generated using the OD readings from the serial dilutions of the BSA standard.

EXAMPLE 6

Microplate Assay for β-galactosidase Expression in Tissues

Tissue was homogenized in an appropriate volume of homogenization buffer (250 mM Tris/5 mM EDTA) (e.g., 300 μL were used to homogenize a mouse lung). The homogenate was then incubated on ice for 30 min and centrifuged in a microcentrifuge for 10 min at 13,000 rpm to clear the homogenate of insoluble debris. Supernatants from these homogenates were collected and assayed as follows.

Microplates were prepared for these analyses as follows. For each plate to be covered, 50 μL of anti-β-galactosidase monoclonal antibody was diluted in 5 mL of 5 mM sodium bicarbonate buffer (pH 9.4). 50 μL of the diluted antibody solution was added to each well of a microtiter plate (e.g., Immulon 3, Dynatech), the plate sealed and incubated overnight at 4° C. After overnight incubation, 200 μL BLOTTO solution (5% v/v nonfat dry milk and 0.2% Tween-20 in PBS) were added to each well and incubated for 1 h at room temperature. The BLOTTO solution was then removed and the plates washed three times with a solution of PBS/0.2% Tween-20, with the exception that the first row was not washed with this solution. 100 μL of a standard solution of 10 mU/mL β-galactosidase were added to the first well of the first row (i.e., well A1) and 100 μL of each tissue extract were added to the other wells in the row. Serial dilutions at ratios of 1:2 were made in each of the adjoining rows consecutively using the wells in the preceding row. Typically, 96-well plates having 12 wells/row resulted in 6 serial dilutions (1 to 1/64); the last row is a blank loaded with PBS as a control. The plates were incubated at room temperature for 1 h, and then washed three times with a solution of PBS/0.2% Tween-20 as above.

To develop the assay, 100 μL of CPRG assay buffer (2.5 mg/mL chlorphenol red-β-$_D$-galactopyranoside monosodium salt (CPRG)/ 1.8 mg/mL $MgCl_2$/7.1 μL/mL 2-mercaptoethanol in PBS) were loaded into each washed well and the plates then incubated at 37° C. for 2 h. The extent of β-galactosidase expression was then determined spectrophotometrically as absorbance at 562 nm.

Whole tissues and tissue sections were assayed using a modification of this protocol. Frozen tissue or tissue sections were fixed by immersing the frozen tissues in fixative solution (2% neutral buffered formalin/0.02% glutaraldehyde/0.02% NP-40) without thawing. Tissues were incubated in fixative solution for 2 h at room temperature with gentle agitation. After incubation, the tissues were rinsed twice with PBS, then incubated at 37° C. overnight in X-Gal staining solution (5 mM potassium ferricyanide/5 mM potassium ferrocyanide/0.01% sodium desoxycholate/ 0.02% NP-40/1 mg/mL X-Gal in PBS, supplemented with $MgCl_2$ to 20 μM immediately before use). After staining, tissues were washed twice with PBS, and then embedded in paraffin or quick frozen for sectioning and histochemical analysis.

EXAMPLE 8

Detection of Functional CFTR Expression in Transfected Cells Using a Chloride Efflux Assay A chloride ion efflux assay was used to detect functional expression of CFTR in transfected cells.

About 24 h prior to introducing CFTR into cells, cells were split into a 6-well tissue culture dish, each well receiving 1 mL of 10 mL of the cells on the dish and 3 mL media. Cells were returned to the incubator and allowed to grow overnight at 37° C./5% $CO_2$, or until they were about 70–80% confluent. For assay, media were removed from the wells and each well was washed with 2 mL serum-free media. 1 mL of serum-free media was then added per well, and the cells incubated at 37° C. for 1–2 h. 200 μl of a DNA-lipid complex comprising a recombinant expression construct encoding CFTR were then added to each well and incubated at 37° C. for 6–8 h. After this incubation, media were removed from each well, the wells were washed twice with 2 mL serum-free media and incubated in 4 mL serum-containing media at 37° C. for 48 h.

The chloride ion efflux assay was performed as follows. Media were aspirated from each of the wells containing cells treated with DNA-lipid complexes, and washed twice with efflux solution (135 mM NaCl/2.4 mM $K_2HPO_4$/0.6 mM $KH_2PO_4$/1.2 mM $CaCl_2$/1.2 mM $MgCl_2$/10 mM glucose/10 mM HEPES (pH 7.4)). Cells were then incubated with 1 mL efflux solution containing $Na^{36}Cl$ at a final concentration of 2.5 μCi/mL $^{36}Cl^-$ for 2 h at 37° C. After incubation, the $^{36}Cl^-$-containing efflux solution was aspirated from the cells and the cells then washed each of 4 times with 1 mL efflux solution. The cells were then incubated with 1 mL efflux solution for 3 min at room temperature, and the efflux solution then removed from the cells and transferred into a scintillation vial containing 5 mL scintillation cocktail. A fresh aliquot of efflux solution was added to each well and incubated for an additional 3 min. After each incubation, efflux solution was transferred to a scintillation vial containing 5 mL scintillation cocktail, and a fresh 1 mL aliquot of efflux media was added to the cells and incubated for 3 min. These steps of the assay were repeated ten times for a total of 30 min. In certain of the wells, $^{36}Cl^-$ ion efflux was stimulated by incubating these cells in the presence of 40 μM Forskolin (Sigma), 500 μM cpt-cAMP (Sigma), and 100 μM IBMX (Sigma) in efflux solution, efflux being stimulated at repetitions 3 through 7.

The extent of $^{36}Cl^-$ ion efflux over this period was determined by scintillation counting, and the basal rate of $^{36}Cl^-$ ion efflux compared with the rate of efflux in cells stimulated by Forskolin/cpt-cAMP/IBMX. Extent of efflux was normalized relative to the amount of $^{36}Cl^-$ ion remaining inside the cells after the 30 min incubation. This quantity was determined by lysing the cells by incubating them with 1 mL of scintillation fluid for 15 min. The lysate from each well was then transferred into a scintillation vial, the well washed with 1 mL of efflux solution which was added to the cell lysate, and the $^{36}Cl^-$ ion-associated radioactivity counted.

The results of one such assay are shown in FIG. 2. Two plasmids encoding CFTR and differing in the details of the construct (see Table I) were tested with (closed circles and boxes) and without (open circles and boxes) stimulation. As is shown in the Figure, stimulation results in the rapid induction of chloride ion efflux over the basal rate of efflux, which efflux persists even after the stimulus is removed (time points 24–30). These results demonstrate the utility of this assay to detect functional expression of CFTR in heterologous cells, and thus forms an in vitro standard for determining the vigor of different recombinant expression constructs in expressing human CFTR.

EXAMPLE 9

Reverse Transcriptase-Polymerase Chain Reaction Analysis

Human CFTR gene expression was assayed using a reverse transcriptase polymerase chain reaction assay (RT-PCR) on transfected tissue culture cells and whole tissues. These assays were performed using vector specific primers and CFTR specific primers. The vector

TABLE I

Vectors with the CFTR cDNA

|        | enhancer | promoter | intron | polyA    | antibiotic |
|--------|----------|----------|--------|----------|------------|
| MB19:  | HCMV     | HCMV     | ppi    | ppi      | amp        |
| MB31:  | HCMV     | HCMV     | ppi    | SV40     | amp        |
| MB65:  | HCMV     | HCMV     | ppi    | Nmyc ppi | amp        |
| MB66:  | HCMV     | HCMV     | ppi    | Cmyc SV40| amp        |
| MB76:  | HCMV     | HCMV     | ppi    | 3xSV40   | amp        |
| MB77:  | —        | CC10     | ppi    | 3xSV40   | amp        |
| MB78:  | HCMV     | CC10     | ppi    | 3xSV40   | amp        |
| MB81:  | —        | CFTR     | ppi    | 3xSV40   | amp        |
| MB87:  | HCMV     | CFTR     | ppi    | 3xSV40   | amp        |
| MB90:  | HCMV     | HCMV     | —      | 3XSV40   | amp        |
| MB93:  | HCMV     | HCMV     | pg13   | SV40     | amp        |
| MB97:  | HCMV     | HCMV     | pg13   | SV40     | amp/tet    |
| MB113: | HCMV     | HCMV     | pg13   | SV40     | tet        | specific primers used were:

5' AGA TCG CCT GGA GAC GCC AT 3'
and
5' GCT CCT AAT GCC AAA GGA AT 3' forward primer
(3651–3671 bp in pMB19)

reverse primer
(1246–1266 bp in pMB19, upstream from hCFTR ATG site).

The CFTR specific primers were used:

5' CCT GTC TCC TGG ACA GAA A 3'
and
5' GTC TTT CGG TGA ATG TTC TGA C 3' forward primer
(3337–3355 bp in pMB19)

reverse primer
(3651–3671 bp in pMB19).

Tissues were frozen on dry ice for RT-PCT and stored at −70° C. Tissue samples were homogenized and used directly in this evaluation.

Briefly, RT-PCR was performed by preparing first-strand cDNA from cellular RNA isolated from frozen tissues using standard techniques (see Sambrook et al., ibid.), including specifically the use of random hexamer for priming and MMLV-derived reverse transcriptase. cDNA was used in PCR reactions performed as follows. The entire 25 μL of the first-strand cDNA reaction was mixed with the components of the PCR reaction (under standard conditions; see Innis et al., 1990, *PCR Protocols: A Guide to Methods and Applications,* Academic Press, New York), including 25 μM apiece of each of the specific pairs of PCR primers. PCR reactions were overlayed with light mineral oil to prevent condensation and then subjected to the following PCR cycling protocol:

| 1 cycle   | 10 min 94° C. |
|-----------|---------------|
| 30 cycles | 1 min 94° C.  |
|           | 2 min 55° C.  |
|           | 3 min 72° C.  |
| 1 cycle   | 10 min 72° C. |
|           | 2 min 27° C.  |

After completion of the reaction, the apparatus was programmed to take and hold the reaction mixtures at 4° C.

PCR products were analyzed by electrophoreses in agarose or acrylamide gels. In these assays, the vector-specific primers were expected to yield a band representative of plasmid DNA (485 bp) and a hCFTR RNA-specific band (142 bp). The CFTR-specific primers were expected to yield a DNA fragment band of 334 bp.

EXAMPLE 10

Functional Delivery of CAT Gene Constructs to Cells In Vivo

Functional delivery of a variety of CAT reporter gene constructs was achieved using different embodiments of the DNA:lipid complexes of the invention.

A. DOTIM:Cholesterol Formulation I

DOTIM:cholesterol liposomes were prepared as described above in 1:1 ratio and used to prepare DNA:lipid complexes. DOTIM:cholesterol (1:1) liposomes were used to make DNA complexes using the chloramphenicol acetyl transferase (CAT) expression vector 4119 (FIG. 3).

DNA:lipid complexes were prepared having a DNA:lipid ratio was 1:6, and using 125 μg of DNA per 200 μL complex. Liposome size was determined by optical density (OD) at 400 nm. A total of 200 μL of the complex were injected into the tail veins of 3 ICR mice. At 24 hrs post-injection, tissues were harvested and prepared for CAT assays as described in Example 4 above. Tissues harvested included lung, liver, kidney, spleen, ovary, brain, smooth muscle, heart and ear.

Results of these CAT assays are shown in Tables II and III below. Table II shows CAT activity as total $^{14}$C-labeled chloramphenicol counts converted to acetyl and diacetyl forms by CAT expression vector-encoded enzyme activity in lung for each of the three experimental animals tested.

TABLE II

| animal number | CAT (cpm) |
|---|---|
| 20.1-1 | 800,000 |
| 20.1-2 | 1,400,000 |
| 20.1-3 | 400,000 |

Table III shows CAT assay data from a variety of tissues from one of the experimental animals (animal 20.1-2). These results demonstrate that intravenous inoculation of mice in the tail vein with DOTIM:cholesterol:DNA complexes in this formulation results in preferential targeting of the DNA:lipid complexes to the lungs, with CAT activity in lung tissue representing over 80% of the CAT activity detected in all mouse tissues tested.

TABLE III

| tissue | CAT (cpm) |
|---|---|
| li | 20,000 |
| sp | 63,000 |
| ki | 15,000 |
| ov | 3,000 |
| br | 7,000 |
| sm | 58,000 |
| he | 115,000 |
| ear | 1500 |

Key:
liver (li),
kidney (ki),
spleen (sp),
ovary (ov),
brain (br),
smooth muscle (sm),
heart (he).

Figure 4:
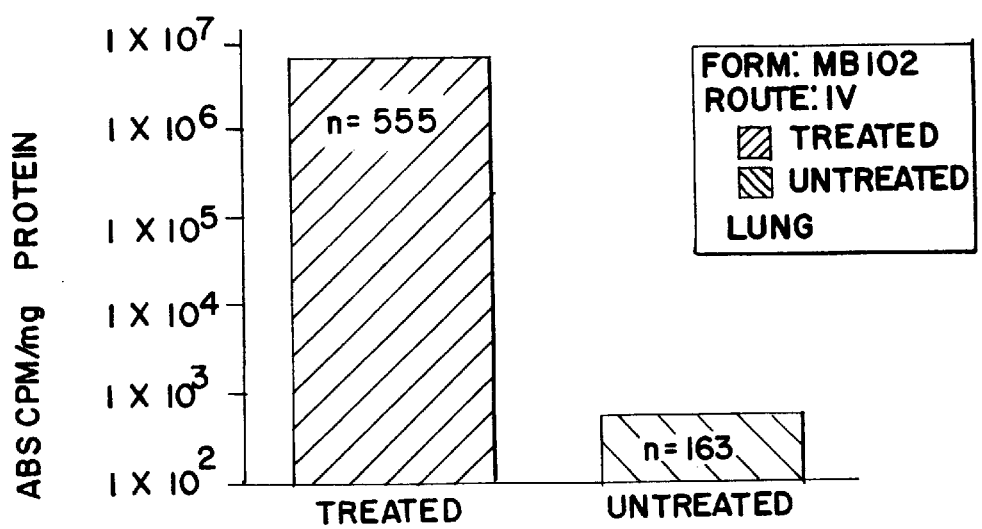
FIG. 4 is a histogram showing that mice administered CAT-encoding plasmids complexed with DOTIM cholesterol liposomes exhibited CAT gene expression in the lung.

The results of these experiments are also shown graphically in FIG. 4, which summarizes the results obtained with over 700 experimental and control mice. As can be seen in the Figure, treated mice reproducibly showed greater than 1000-fold higher CAT activity in lung of mice treated with the DNA:lipid complexes of the invention comprising CAT-encoding recombinant expression constructs (a total of 555 mice), compared with control (untreated) mice (a total of 163 mice).

The delivery and uptake into cells of various mouse tissues of the CAT plasmid DNA administered as DNA:lipid complexes of the invention by injection into the tail vein of mice was analyzed by Southern blot analysis using routine procedures (see Sambrook et al. ibid.). DNA from mouse tissues was extracted and purified and digested with BammI restriction endonucleases. The resulting DNA restriction fragments were separated by agarose gel electrophoresis and transferred to a membrane by capillary action. Such membranes were dried, prehybridized and then hybridized with a radioactively-labeled, CAT DNA-specific probe (about 108–109 dpm/μg) at an appropriate stringency (2X–6X SSC at 62° C.) overnight, washed to high stringency (0.1–0.5X SSC at 65° C.) and exposed to autoradiographic film at −70° C. using intensifying screens.

Figure 5:
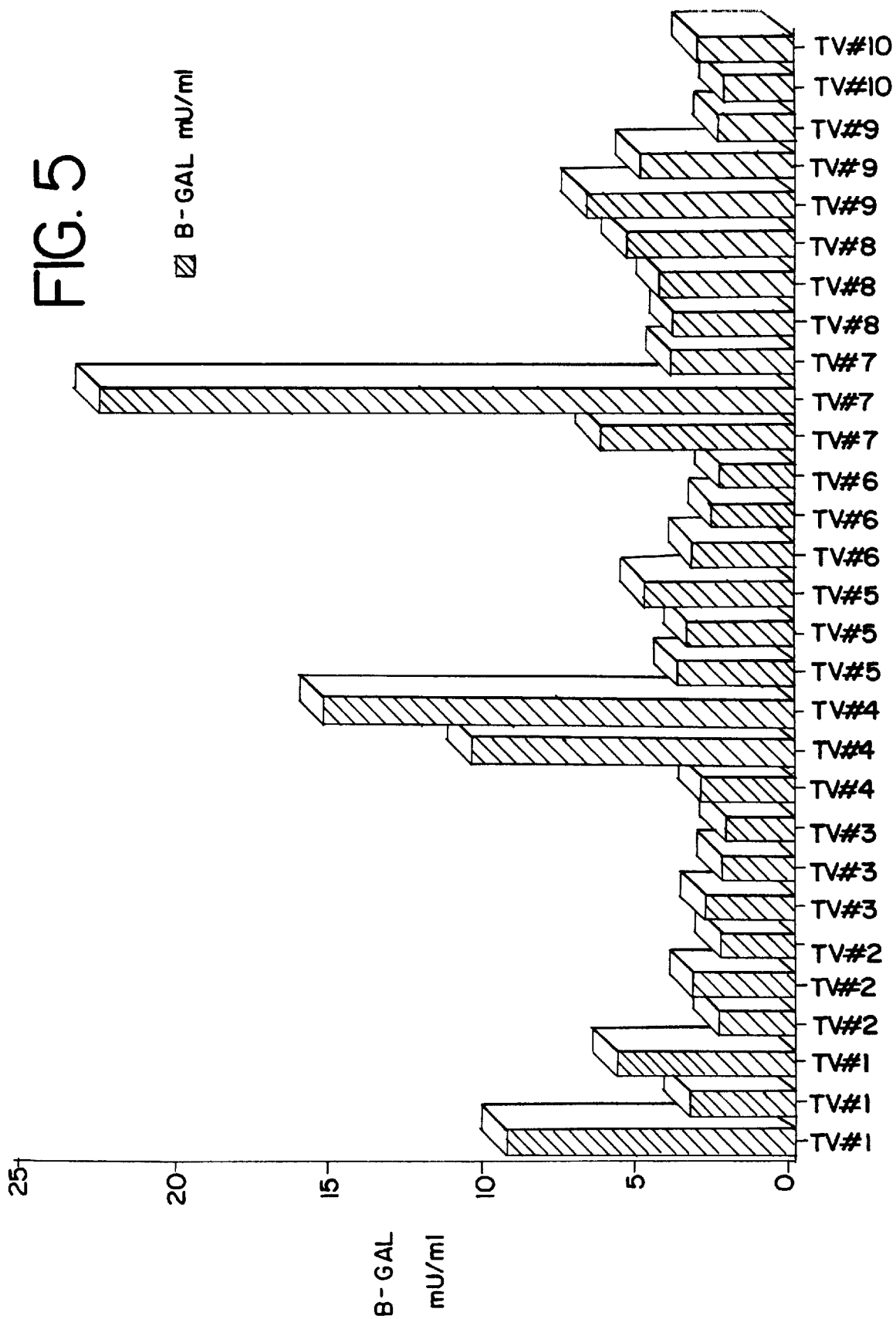
FIG. 5 is a histogram showing β-galactosidase expression in mouse lung in 9 experimental mice administered β-galactosidase-encoding DNA:liposome complexes of the invention.

Results of these experiments are shown in FIG. 5. The lower panel is identical to the upper panel, but has been allowed to expose the X-ray film for a longer period of time. These results of these experiments demonstrate that CAT DNA is introduced specifically into lung, with significant amounts of DNA uptake in spleen. Much lower amounts of CAT DNA were observed in certain other tissues (liver, kidney) but many tissues showed essentially no CAT-specific hybridization, even at the longer exposure time.

A second series of experiments were performed using this lipid formulation. In these experiments, the DNA construct used was the β-galactosidase expression vector MB10 (see Table I) that encodes a form of β-galactosidase that is translocated into the nucleus in in vitro studies. Complexes were formed as described above, and mice were injected with 200 μL complexes in the tail vein. The resulting β-galactosidase levels present in lungs are shown in FIG. 5, which represents the results of experiments with 9 experimental and 1 control (administered liposome only) mouse.

Figure 6:
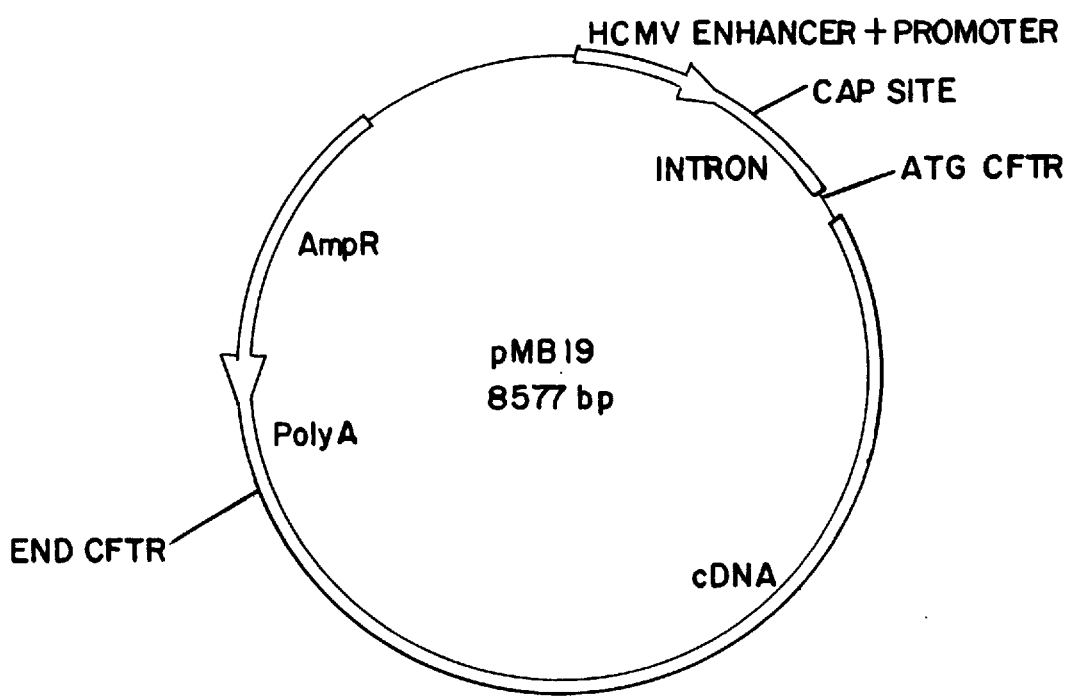
FIG. 6 is a schematic representation of the plasmid pMB19.

In a third series of experiments, expression of the human CFTR gene was shown following IV delivery of DNA/DOTIM:Cholesterol complexes. A recombinant expression plasmid encoding the human CFTR gene (MB19; see Table I and FIG. 6) was used to make DNA:lipid complexes as described above (DNA/lipid ratio of 1:6, 125 μg DNA /200 μL complex). These complexes were tested by transfection/chloride ion efflux assay in human 293 cells in vitro, as described in Example 8, and 200 μL was injected into each of ICR 3 mice. Cells and lungs were harvested at 24 hrs. RNA was made using conventional methods as embodied in kits from either Stratagene (for cell culture results) or 5'-3' Prime (for lung tissues). Samples were analyzed by RT-PCR as described above in Example 9. In this analysis, amplification of plasmid sequences yielded a 484 bp PCR product, while amplification of cDNA corresponding to spliced CFTR mRNA for CFTR yielded a 142 bp PCR product. Similar results were obtained from lungs following IV administration of the CFTR/lipid complexes.

Figure 7:
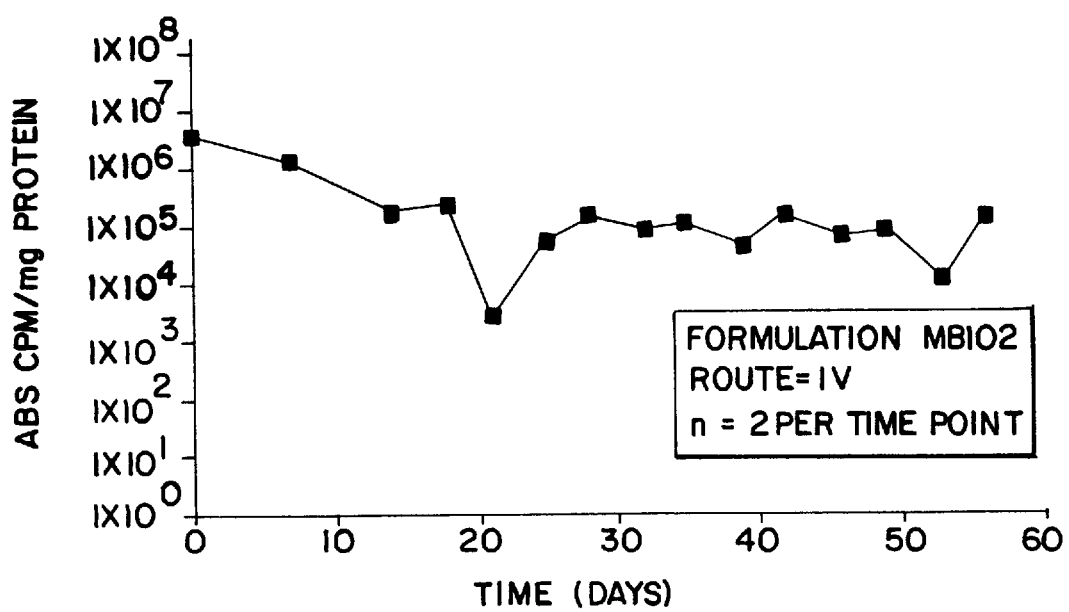
FIG. 7 is a graph showing long-term, persistent expression of CAT activity in mouse lung obtained after intravenous administration of CAT-encoding DNA:liposome complexes of the invention.

The time course of expression of exogenously added CAT-encoding plasmid in mouse lung was determined. A number of mice were injected intravenously in the tail vein with DNA/lipid complexes comprising 4119 CAT DNA at a 1:6 ratio with DOTIM:Cholesterol at a concentration of 125 μg/200 μl. Mice were sacrificed in duplicate over a period of 55 days, and lung tissue analyzed by CAT assay as described above. These results are shown in FIG. 7, which indicated that high-level, persistent expression of the reporter gene construct had been achieved.

Figure 8:
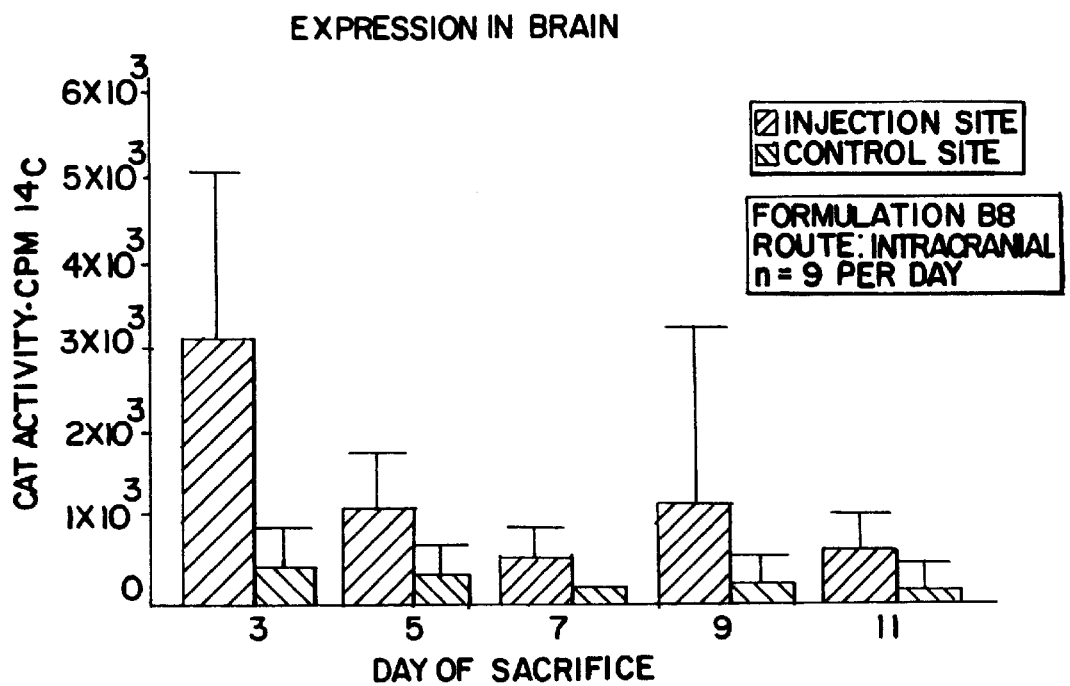
FIG. 8 is a histogram showing CAT gene expression in brain after CAT-encoding DNA:liposome complexes of the invention were administered intracranially.

Complexes of this DOTIM:DNA formulation were also administered by direct intracranial delivery. Complexes were made using CAT expression plasmid 4119 and complexed with DOTIM:Cholesterol (1:1) at a ratio of 1:1 DNA:lipid at a DNA concentration of 500 μg/200 μL. 200 μL of these complexes were directly implanted intracranially, and the extent of CAT activity is brain tissue analyzed 24 h later. The results of these experiments are shown FIG. 8.

The results of these different assays indicated that this DOTIM:Cholesterol formulation was capable of delivering a variety of recombinant expression constructs to the lung after intravenous administration, as well as by direct injection into a tissue of interest (brain).

B. DOTIM:Cholesterol Formulation II

DOTIM:cholesterol liposomes were prepared as described above in 1:1 ratio and used to prepare DNA:lipid complexes. DOTIM:cholesterol (1:1) liposomes were used to make DNA complexes using the chloramphenicol acetyl transferase (CAT) expression vector 4119. DNA:lipid complexes were prepared having a DNA:lipid ratio was 1:1, and using 200–550 μg of DNA per 200 μL complex. Liposomes were injected into the tail vein of ICR mice, as described above.

CAT gene expression in lung tissue from mice injected with DOTIM:Cholesterol:DNA complexes prepared at a DNA/lipid ratio of 1:1 was determined. Plasmid 4119 DNA was complexed with DOTIM:Cholesterol formulation of the invention, the complexes having a DNA/lipid ratio of 1:1. Tail vein injections were performed and tissues harvested at 24 hrs as described.

The results of these assays are shown in Table IV below.

TABLE IV

| Amount of DNA/complex | OD$_{400}$* | lung expression** |
| --- | --- | --- |
| 200 μg/200 μl | 0.24 | 39,000 |
| 300 μg/200 μl | 0.32 | 9,000 |
| 400 μg/200 μl | 0.53 | 500,000 |
| 500 μg/200 μl | 0.66 | 700,000 |
| 550 μg/200 μl | 0.82 | 1,000,000 |
| negative control | 0.03 | 0 |

*light scattering as an estimate of liposome size
**in cpm of acetylated and diacetylated $^{14}$C-labeled chloramphenicol DNA/DOTIM liposomes were made using the plasmid 4119 and DOTIM liposomes at ratios of 1:6 and 1:8, were held at 40° C. for 11 days prior to testing and then tested again at 18 days. The results of CAT expression assays using these formulations are shown in Table V.

TABLE V

| DNA/DOTIM ratio | time stored | CAT/lung** |
| --- | --- | --- |
| 1:6 | 11 days | 515,000 |
| 1:8 | 11 days | 1,050,000 |
| 1:6 | 18 days | 11,000,000 |
| 1:8 | 18 days | 3,450,000 |

**in cpm of acetylated and diacetylated $^{14}$C-labeled chloramphenicol

Figure 9:
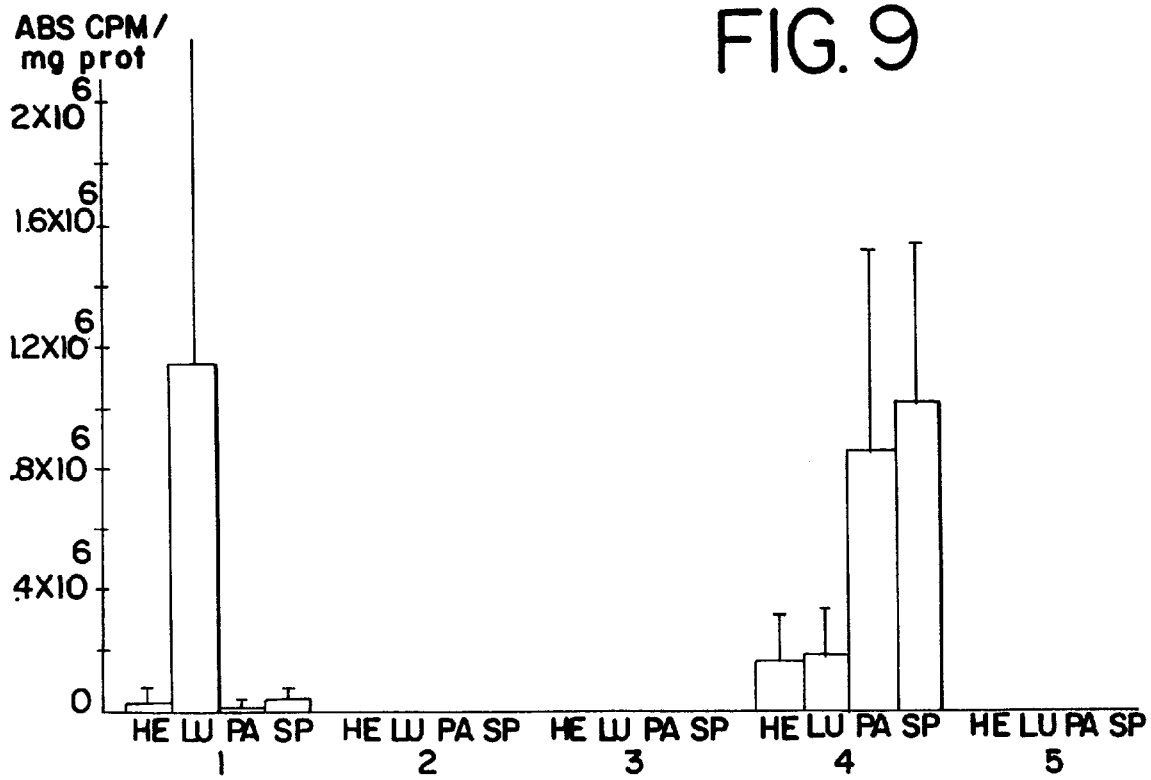
FIG. 9 is a histogram comparing tissue specificity of CAT gene expression in DNA:liposome complexes administered intravenously (samples 1 and 2) or intraperitoneally (samples 4 and 5).

DOTIM:cholesterol complexes with DNA were also administered by intraperitoneal injection. DNA:liposome complexes administered intravenously and intraperitoneally were compared, using CAT expression plasmid 4119 DNA complexed with DOTIM:Cholesterol formulation of the invention. In these assays, the complexes had a DNA/lipid ratio of 1:1 and a DNA concentration of 300–500 μg/200 μL. A total of 1 mL of these complexes was injected intraperitoneally in two mice (mice 4 and 5), 200 μL were administered intravenously (mice 1 and 2), and 1 mouse was administered a formulation comprising only liposomes. Tissues were harvested at 48 h post-injection. CAT assays were performed as described above in Example 3, and the results of these assays are shown in FIG. 9.

The effect on the efficiency of DNA delivery to tissues in vivo of intravenously administering different formulations comprising the same mixture of cationic and neutral lipids was determined by comparing the extent of transferred CAT activity observed using the different formulations. CAT plasmid DNA/DOTIM:DOPE (1:1) complexes were prepared in the following formulations:

A. DNA:Lipid ratio of 1:6 DNA concentration of 0.625 mg/mL
B. DNA:Lipid ratio of 1:1 DNA concentration of 2.5 mg/mL Each formulation was prepared as described in Examples 1 and 3 above, and were administered by intravenous injection into the tail vein of cohorts of 3 ICR mice per tested formulation. Liposomes that were not complexed with DNA were injected into a separate cohort of 3 mice as a control.

Figure 10:
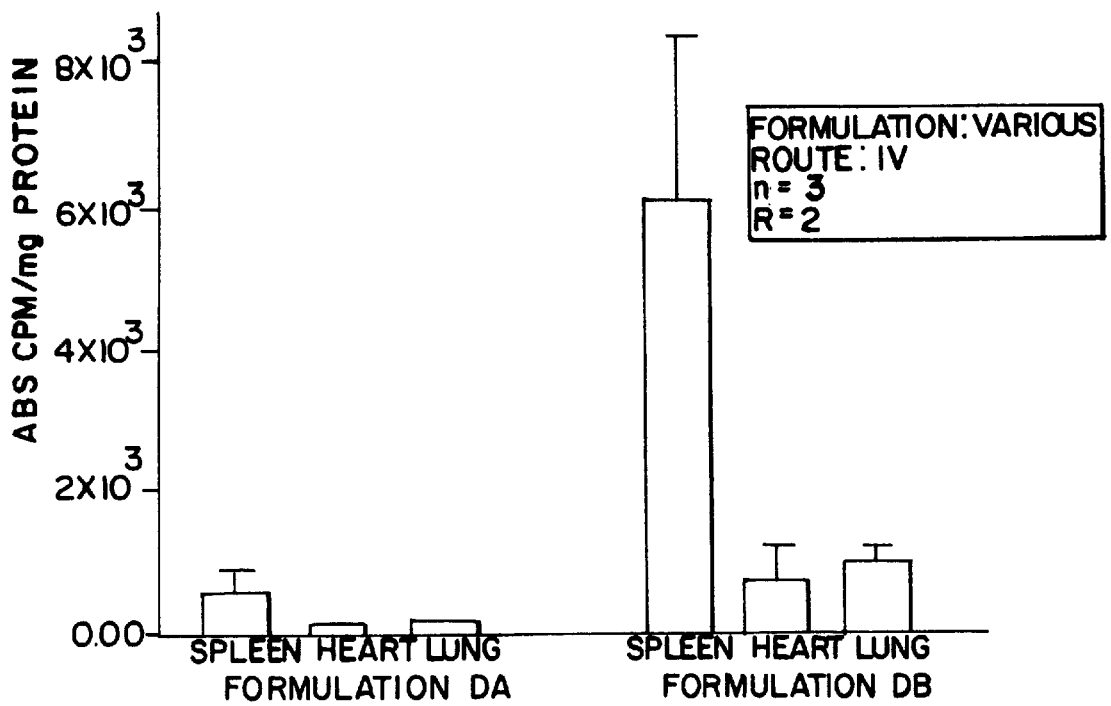
FIG. 10 is a histogram showing formulation-dependent variability in the extent of spleen expression of CAT after intravenous administration of DNA:liposome complexes of the invention.

Animals were sacrificed 1–2 days after injection and analyzed by CAT assay of spleen, heart and lung tissue. The results of these experiments are shown in FIG. 10. This Figure demonstrates that Formulation B provides a consistently higher level of CAT activity in spleen, heart and lung than Formulation A, although it appears that the relative efficiency of plasmid delivery is about the same for both formulations.

C. Comparison of HLA Gene Delivery using Different DNA:Lipid Complexes

Three different lipid formulations were used to deliver a human HLA-encoding construct to bone marrow, spleen and lymph node. The three formulations used were:

A. DOTIM:Cholesterol (1:1) DNA:Lipid ratio of 1:6 DNA concentration of 0.625 mg/mL
B. DOTIM:Cholesterol (1:1) DNA:Lipid ratio of 1:1 DNA concentration of 2 mg/mL
C. DOTIM:DOPE (1:1) DNA:Lipid ratio of 1:1 DNA concentration of 2 mg/mL (DOPE is dioleoylphosphatidylethanolamine). Each formulation was prepared as described in Examples 1 and 3 above, and were administered by intravenous injection into the tail vein of cohorts of 3 ICR mice per tested formulation. Liposomes that were not complexed with DNA were injected into a separate cohort of 3 mice as a control.

Figure 11:
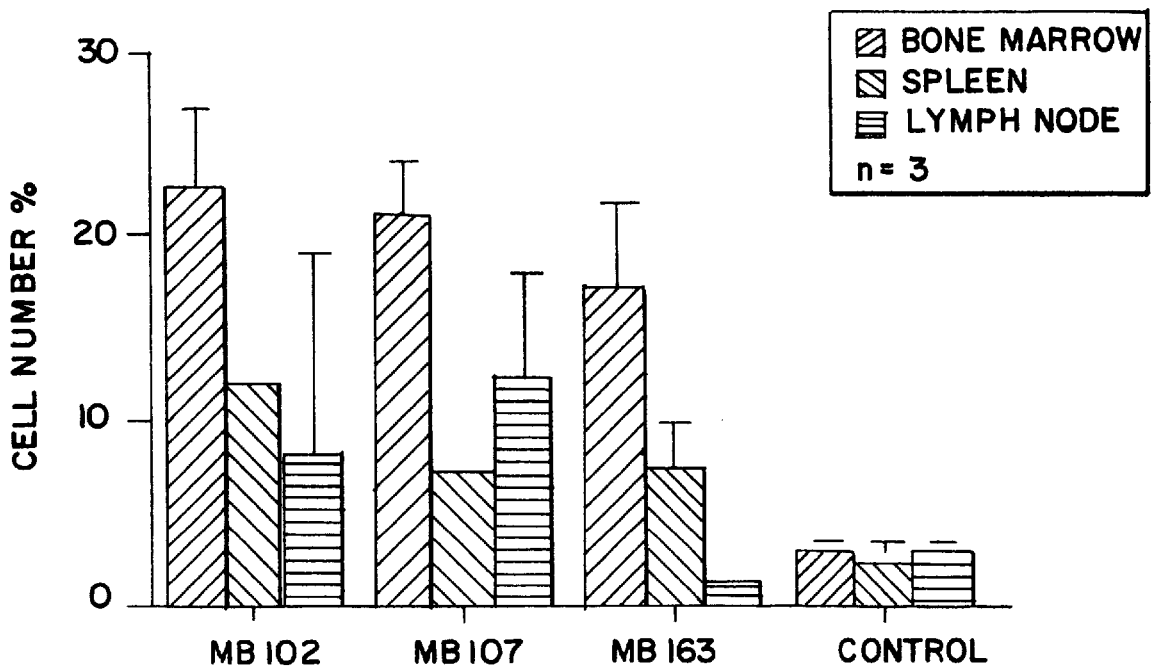
FIG. 11 is a histogram showing human HLA antigen expression in bone marrow, spleen and lymph nodes following intravenous administration of various formulations of DNA:liposome complexes of the invention.

Animals were sacrificed 1–2 days after injection and analyzed by histochemical staining for human HLA expression. Tissues were analyzed for percentage of cells in the tissue positive for human HLA expression in the histochemical staining assay. Results of these experiments are shown in FIG. 11, wherein Formulation A is MB102, Formulation B is MB107 and Formulation C is MB163. For each formulation tested, some cells in each tissues were found to stain positive for human HLA expression. Lymph node staining varies most among different administered formulations, with DOTIM:Cholesterol at the higher (2 mg/mL) DNA concentration providing the most human HLA positive cells, and the DOTIM:DOPE formulation providing the least human HLA positive cells. The results in spleen were less variable, with the DOTIM:Cholesterol formulation at the lower (0.625 mg/mL) DNA concentration providing the most human HLA positive cells. Bone marrow cells showed high levels of human HLA positive cells with all formulations tested.

In view of these results, a series of experiments were performed to demonstrate formulation-dependent targeting of DNA:lipid complexes to spleen and lung. Two formulations were used:

a. DOTIM:Cholesterol (1:1) DNA:Lipid ratio of 1:6 DNA concentration of 0.625 mg/mL
b. DOTIM:DOPE (1:1) DNA:Lipid ratio of 1:1 DNA concentration of 1.5 mg/mL Each formulation was prepared as described in Examples 1 and 3 above, using a CAT-encoding construct, and were administered by intravenous injection into the tail vein of cohorts of 3 ICR mice per tested formulation. Liposomes that were not complexed with DNA were injected into a separate cohort of 3 mice as a control.

Figure 12:
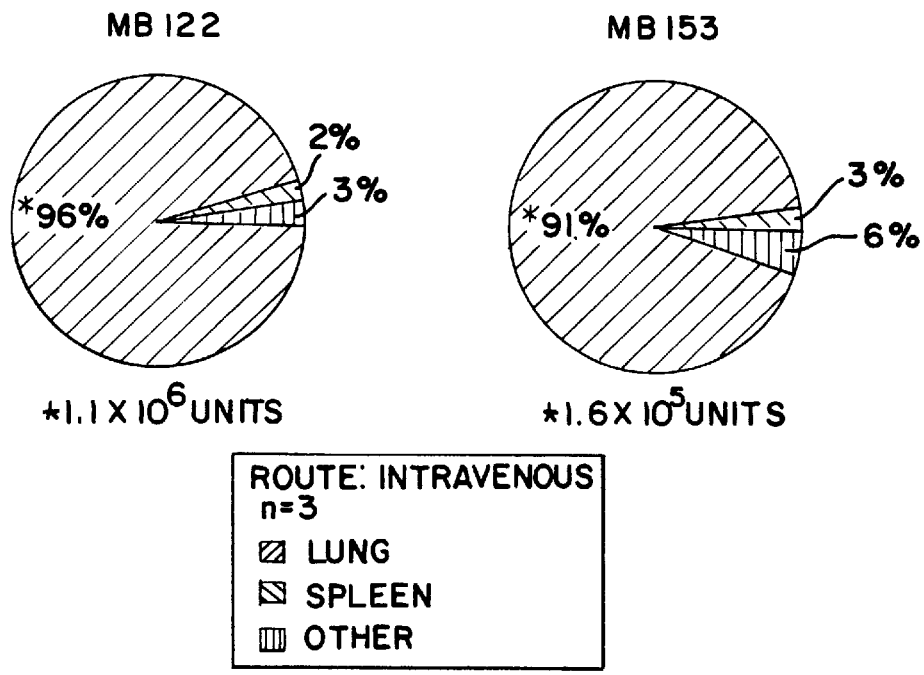
FIG. 12 is a representation of tissue-specific targeting of CAT-encoding DNA complexed with different liposome complexes and administered intravenously.

Animals were sacrificed 1–2 days after injection and analyzed by CAT assay of lung and spleen tissues as described above. The results of these experiments are shown in FIG. 12. CAT activity is expressed as the percentage of total $^{14}$C-chloramphenicol counts converted to acetylated and diacylated forms associated with each tissue. As can be seen from the Figure, the DOTIM:Cholesterol formulation administered intravenously resulted in 96% (of over 1 million counts) being localized to lung tissue; 2% of the counts resulting from this formulation were found in the spleen, and the rest were found in other tissues. In contrast, the DOTIM:DOPE formulation administered intravenously resulted in 91% (of 160,000 counts) being localized to spleen tissue, with about 3% of the counts being found in the lung and the rest being found in other tissues. These results demonstrate that this DOTIM:Cholesterol formulation specifically targets the DNA:lipid complex to the lung, while the DOTIM:DOPE formulation specifically targets DNA:lipid complexes to the spleen. In addition, these results show that CAT activity is about 10-fold more robust when delivered in DOTIM:Cholesterol complexes to the lung that the CAT activity resulting from DOTIM:DOPE complex-mediated delivery to spleen.

D. Intraperitoneal Delivery Formulations

Liposome formulations were developed for targeted gene delivery by intraperitoneal administration. DOTIM:Cholesterol formulations (1:1) were tested using a CAT-encoding construct at a DNA:lipid ratio of 1:1 and a total DNA concentration in the complex of 2.5 mg/mL. 1 mL of these DNA complexes were injected into the peritoneal cavity of each of 4 mice; an equal volume of the liposome formulation not complexed with CAT-encoding DNA was injected into 4 mice in a separate cohort as a control. Peritoneal macrophages were isolated 24–48 h after injection and tested for CAT activity as described above.

Figure 13:
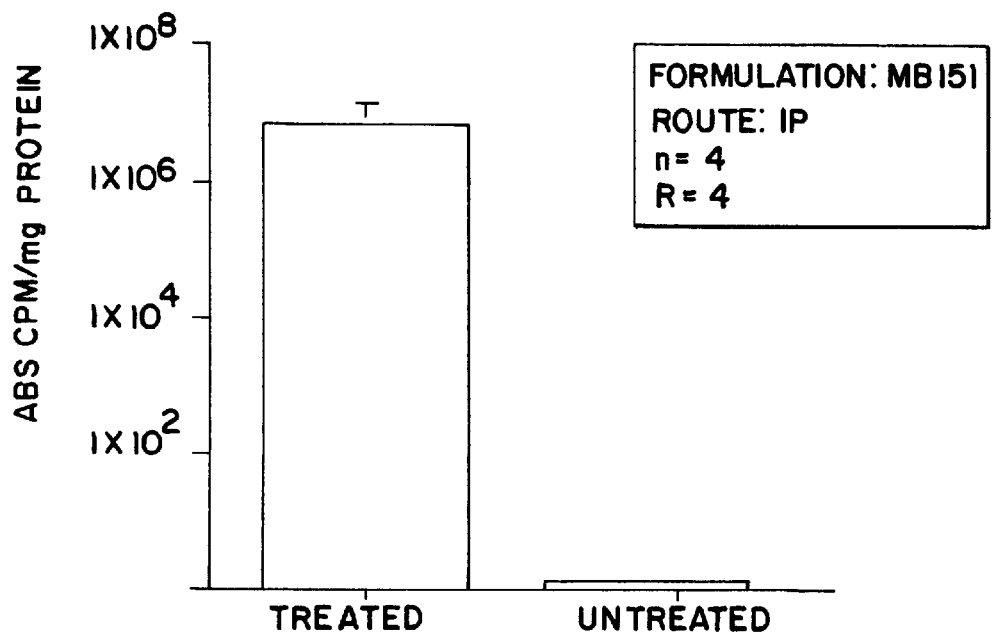
FIG. 13 is a histogram illustrating CAT gene targeting to peritoneal macrophages after intraperitoneal injection.

The results of these experiments are shown in FIG. 13. Peritoneal macrophages from control (untreated) mice showed essentially no CAT activity in this assay. Macrophages from mice administered the DNA:lipid complexes in this formulation intraperitoneally showed high levels of CAT activity, demonstrating specific in vivo delivery of a functional CAT gene using this formulation.

Figure 14:
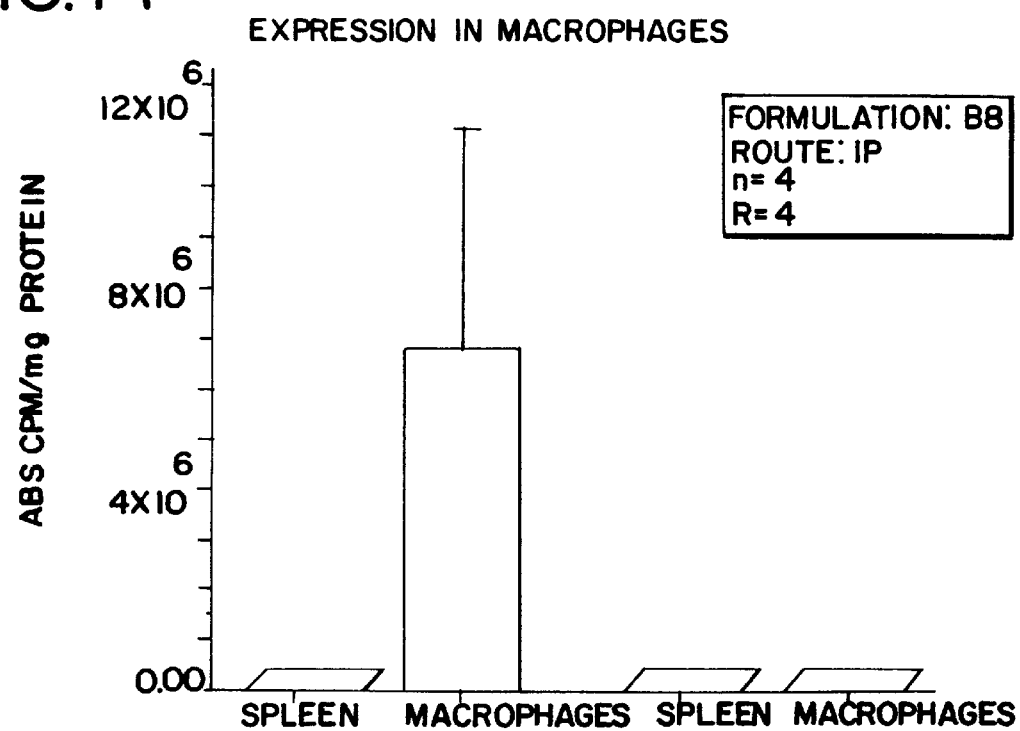
FIG. 14 is a histogram showing macrophage-specific targeting by administration of CAT-encoding DNA using DNA:liposome complexes of the invention.

Spleens from these animals were also tested and CAT activity compared to peritoneal macrophages. These results are shown in FIG. 14, where it can be seen that CAT activity in macrophages was much higher than in spleen, demonstrating specificity in targeting to these cells.

Pancreatic tissues were targeted for gene delivery using the DNA:lipid formulations of the invention as follows. A formulation comprising a CAT-expressing plasmid and DOTIM:DOPE (1:1), at a DNA:lipid ratio of 1:1, and a total DNA concentration in the complex of 1.5 mg/mL was injected intraperitoneally into a cohort of 3 mice. Two mice were injected with the liposome formulation not complexed with DNA as a control. Pancreas and lung tissues were analyzed 24–48 h post-administration for CAT activity as described above.

Figure 15:
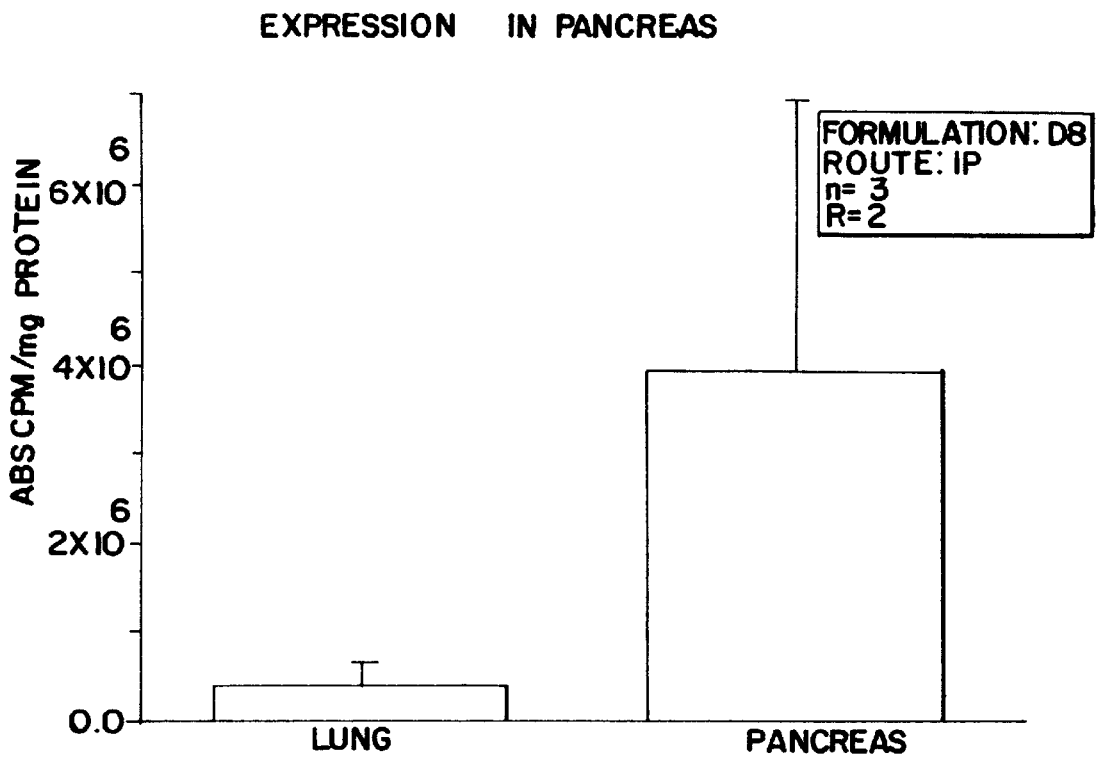
FIG. 15 is a histogram showing pancreas-specific targeting by administration of CAT-encoding DNA using DNA:liposome complexes of the invention.

The results of these experiments are shown in FIG. 15. These results demonstrate that this formulation specifically targets delivery of CAT-encoding DNA constructs to the pancreas when administered intraperitoneally.

A CAT-encoding recombinant construct was targeted to spleen using yet another DNA:lipid formulation. Plasmid DNA was complexed with DOTIM:Cholesterol (1:1), at a DNA:lipid ratio of 1:1, and a total DNA concentration in the complex of 2.5 mg/mL was injected intraperitoneally into a cohort of 3 mice. A separate cohort of mice were injected with the liposome formulation not complexed with DNA as a control. Spleen tissues from mice in each cohort were analyzed 24–48 h post-administration for CAT activity as described above.

Figure 16:
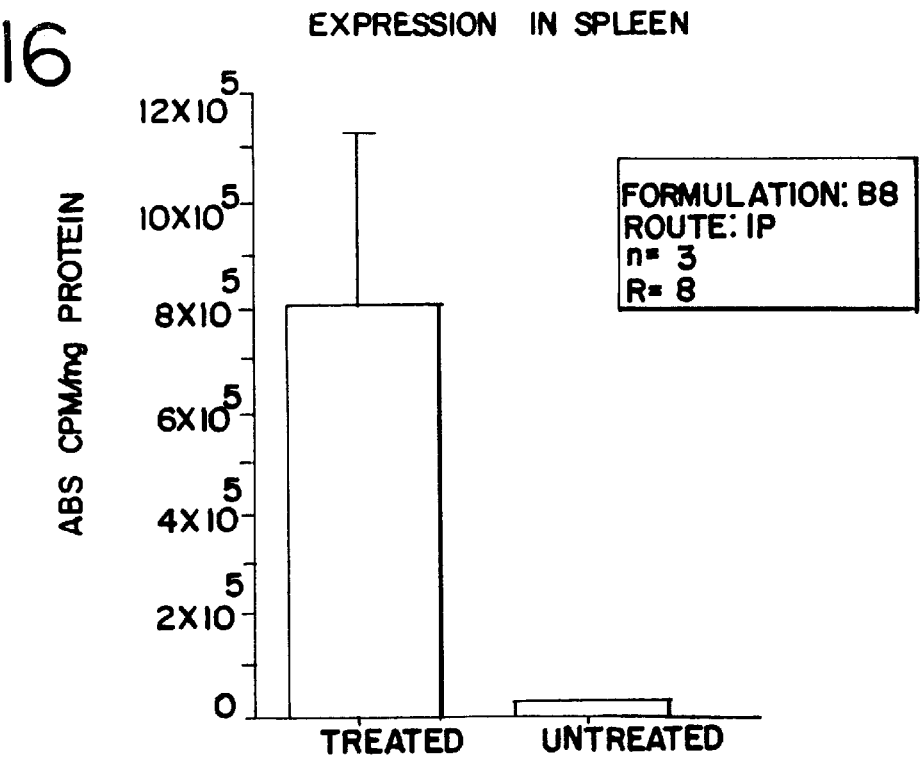
FIG. 16 is a histogram showing spleen-specific targeting by administration of CAT-encoding DNA using DNA:liposome complexes of the invention.

The results of these experiments are shown in FIG. 16. These results demonstrate that this formulation specifically targets delivery of CAT-encoding DNA constructs to spleen in vivo when administered intraperitoneally.

The tissue specificity of intraperitoneal delivery was demonstrated by comparison of two different formulations administered intraperitoneally. The following formulations were tested:

a. DOTIM:Cholesterol (1:1) DNA:Lipid ratio of 1:6 DNA concentration of 0.625 mg/mL
b. DOTIM:DOPE (1:1) DNA:Lipid ratio of 1:1 DNA concentration of 1.5 mg/mL Each formulation was prepared as described in Examples 1 and 3 above, using a CAT-encoding construct, and were administered by intraperitoneal injection into the tail vein of cohorts of 3 ICR mice per tested formulation. Liposomes that were not complexed with DNA were injected into a separate cohort of 3 mice as a control.

Figure 17:
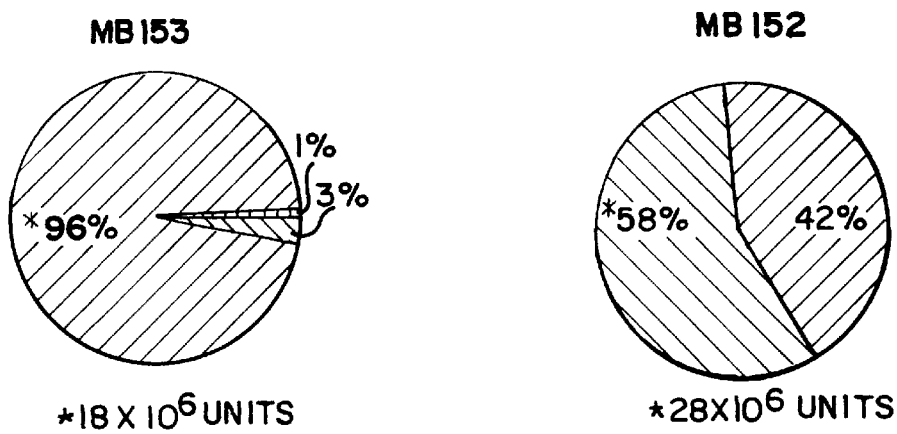
FIG. 17 is a representation of tissue-specific targeting of CAT-encoding DNA complexed with different liposome complexes and administered interperitoneally.

Animals were sacrificed 1–2 days after injection and analyzed by CAT assay of pancreas and spleen tissues as described above. The results of these experiments are shown in FIG. 17. CAT activity is expressed as the percentage of total $^{14}$C-chloramphenicol counts converted to acetylated and diacylated forms associated with each tissue. As can be seen from the Figure, the DOTIM:DOPE formulation administered intraperitoneally resulted in 96% (of 18 million counts) being localized to pancreatic tissue; 3% of the counts resulting from this formulation were found in the spleen, and the rest were found in other tissues. In contrast, the DOTIM:Cholesterol formulation administered intraperitoneally resulted in 58% (of 28 million counts) being localized to spleen tissue, with about 42% of the counts being found in the pancreas; essentially no CAT activity was observed in other tissues. These results demonstrate that this DOTIM:DOPE formulation specifically targets the DNA:lipid complex to the pancreas when administered intraperitoneally, while the DOTIM:Cholesterol formulation specifically targets DNA:lipid complexes to the pancreas and spleen.

E. Direct Delivery Formulations

Liposome formulations were developed for targeted gene delivery by direct injection into tissues. DOTIM:Cholesterol formulations (1:1) were tested using a CAT-encoding construct at a DNA:lipid ratio of 1:1 and a total DNA concentration in the complex of 2.5 mg/mL. This formulation was directly injected in 1.5 mL into a human prostate ex corpora, and the assayed by CAT assay as described above.

Figure 18:
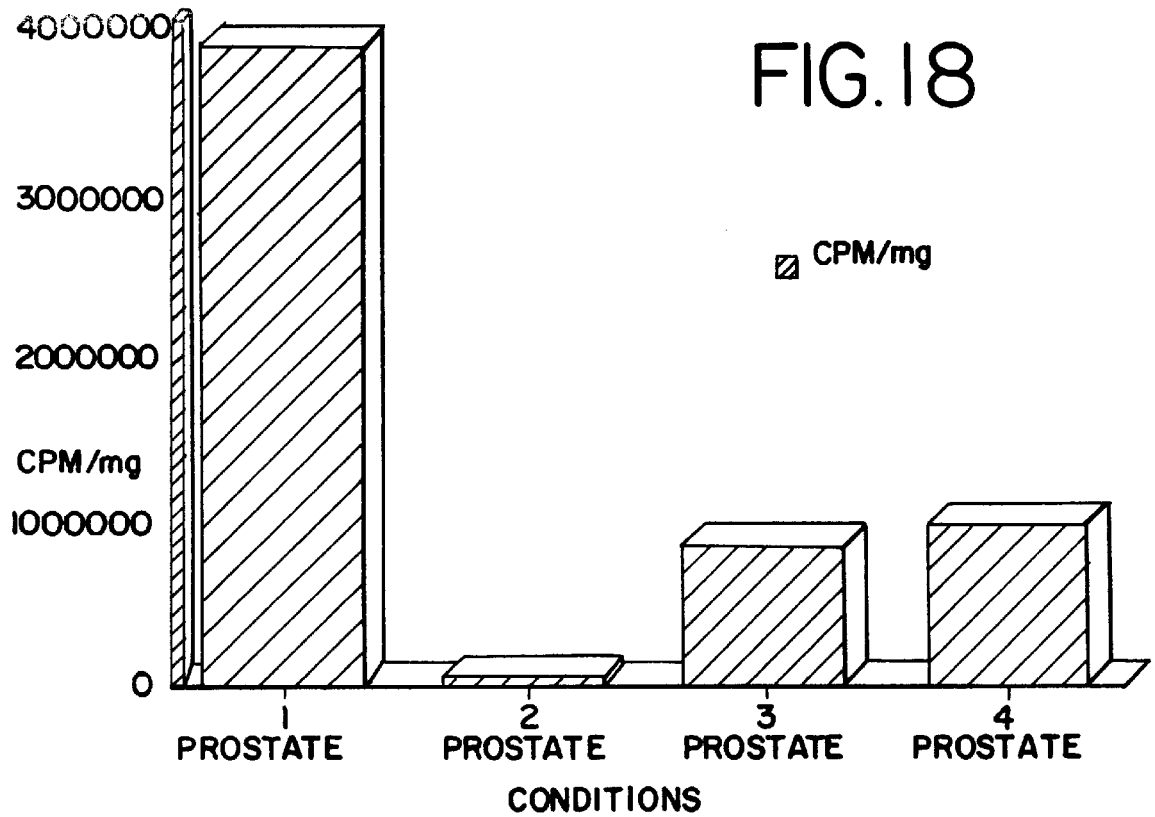
FIG. 18 is a histogram showing CAT gene expression in human prostate tissue in which CAT-encoding DNA using DNA: liposome complexes of the invention were directly administered ex corpora.

The results of this experiment are shown in FIG. 18. These results demonstrate that gene delivery can be mediated by direct injection of DNA:lipid complexes on the invention into human tissues.

F. Comparison of Intravenous and Intraperitoneal Administration Routes

Figure 19:
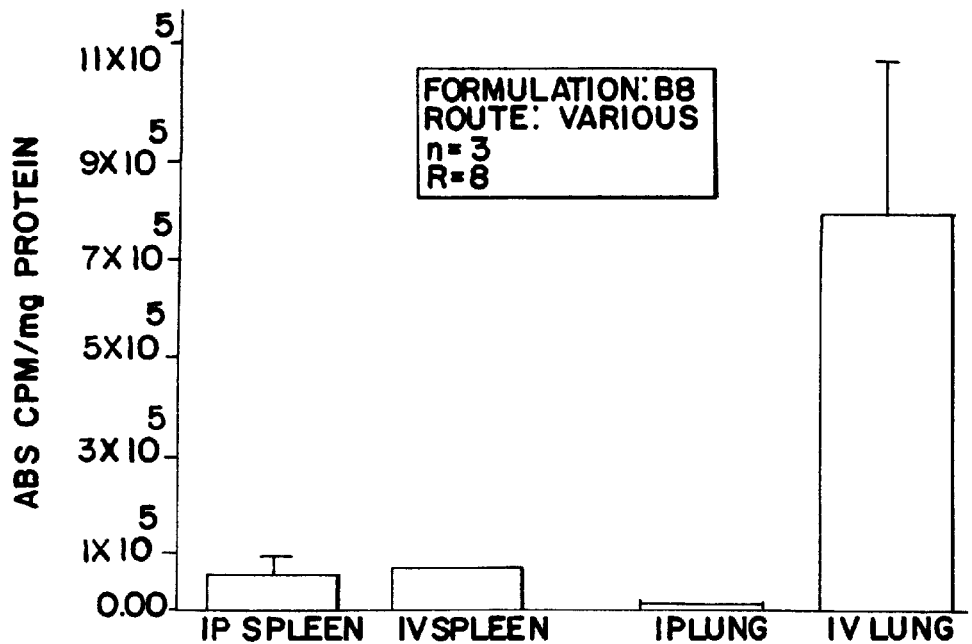
FIG. 19 is a histogram showing a comparison of spleen-specific and lung-specific targeting of DNA:liposome complexes of the invention using intravenous and intraperitoneal routes of administration.

The effect of administration route on targeted delivery of CAT-encoding plasmid DNA using a single DNA:lipid complex formulation was determined. DOTIM:Cholesterol formulations (1:1) were tested using a CAT-encoding construct at a DNA: lipid ratio of 1:1 and a total DNA concentration in the complex of 2.5 mg/mL. Cohorts of 3 mice were either injected intravenously in the tail vein, or intraperitoneally. Spleen and lung tissues were analyzed 24–48 h post-administration for CAT activity as described above. The results of these experiments are shown in FIG. 19. It can be seen from the Figure that the highest CAT activity levels were achieved in lung tissue following intravenous administration of the formulation. However, CAT activity after intraperitoneal administration was relatively higher in spleen than in lung. These results demonstrate that tissue-specific targeting of DNA delivery can be achieved with the same efficacious formulation of DNA:lipid complexes, and that the targeted site can be influenced by the route of administration.

It should be understood that the foregoing disclosure emphasizes certain specific embodiments of the invention and that all modifications or alternatives equivalent thereto are within the spirit and scope of the invention as set forth in the appended claims.

We claim:

1. A pharmaceutical composition comprising a formulation of a complex of a recombinant expression construct and a mixture of a neutral lipid and 1-(2-(oleoyloxy)ethyl)-2-oleoyloxy)ethyl)-2-oleyl-3-(2-hydroxyethyl)imidazolinium chloride as a cationic lipid in a pharmaceutically acceptable carrier suitable for administration to an animal by intravenous, intraperitoneal or direct injection into a tissue in the animal, wherein:

(a) the recombinant expression construct comprises a nucleic acid encoding a protein and wherein said nucleic acid is operatively linked to gene expression regulatory elements whereby the protein encoded by the nucleic acid is expressed in cells in a tissue in an animal; and (b) the cationic lipid and the neutral lipid are present in the complex at a molar ratio of about 1:1, the DNA and the cationic lipid are present in the complex in a ratio of from about 1:1 to about 1:8 µg DNA/nmole cationic lipid, and the nucleic acid comprising the recombinant expression construct is present in the complex at a concentration of about 0.5 mg/mL to about 5 mg/mL.

2. The pharmaceutical composition of claim 1 wherein the neutral lipid is cholesterol or dioleoylphosphatidylethanolamine.

3. The pharmaceutical composition of claim 1 wherein the complex of the recombinant expression construct and a mixture of a neutral lipid and a cationic lipid comprises a ratio of DNA to cationic lipid of about 1:1 µg DNA/nmole cationic lipid.

4. A method of introducing a recombinant expression construct into a cell within a lung in an animal, the method comprising the step of administering the pharmaceutical composition of claim 1 to the animal by intravenous injection, wherein the neutral lipid is cholesterol, the cationic lipid and the neutral lipid are present in a molar ratio of about 1:1, the complex of the recombinant expression construct and a mixture of a neutral lipid and a cationic lipid comprises a ratio of DNA to cationic lipid of about 1:6 µg DNA/nmole cationic lipid, and the DNA concentration in the DNA:lipid complexes is from about 0.5 mg/mL to about 1 mg/mL.

5. A method of introducing a recombinant expression construct into a cell within a spleen in an animal, the method comprising the step of administering the pharmaceutical composition of claim 1 to the animal by intravenous injection, wherein the neutral lipid is dioleoylphosphatidylethanolamine, the cationic lipid and the neutral lipid are present in a molar ratio of about 1:1, the complex of the recombinant expression construct and a mixture of a neutral lipid and a cationic lipid comprises a ratio of DNA to cationic lipid of about 1:1 µg DNA/nmole cationic lipid, and the DNA concentration in the DNA:lipid complexes is from about 1 mg/mL to about 2.5 mg/mL.

6. A method of introducing a recombinant expression construct into a cell that is a peritoneal macrophage in an animal, the method comprising the step of administering the pharmaceutical composition of claim 1 to the animal by intraperitoneal injection, wherein the neutral lipid is cholesterol, the cationic lipid and the neutral lipid are present in a molar ratio of about 1:1, the complex of the recombinant expression construct and a mixture of a neutral lipid and a cationic lipid comprises a ratio of DNA to cationic lipid of about 1:1 µg DNA/nmole cationic lipid, and the DNA concentration in the DNA:lipid complexes is from about 1 mg/mL to about 2.5 mg/mL.

7. A method of introducing a recombinant expression construct into a cell within a spleen in an animal, the method comprising the step of administering the pharmaceutical composition of claim 1 to the animal by intraperitoneal injection, wherein the neutral lipid is cholesterol, the cationic lipid and the neutral lipid are present in a molar ratio of about 1:1, the complex of the recombinant expression construct and a mixture of a neutral lipid and a cationic lipid comprises a ratio of DNA to cationic lipid of about 1:1 µg DNA/nmole cationic lipid, and the DNA concentration in the DNA-lipid complexes is from about 1 mg/mL to about 2.5 mg/mL.

8. A method of introducing a recombinant expression construct into a cell within a pancreas in an animal, the method comprising the step of administering the pharmaceutical composition of claim 2 to the animal by intraperitoneal injection, wherein the neutral lipid is dioleoylphosphatidylethanolamine, the cationic lipid and the neutral lipid are present in a molar ratio of about 1:1 the complex of the recombinant expression construct and a mixture of a neutral lipid and a cationic lipid comprises a ratio of DNA to cationic lipid of about 1:1 µg DNA/nmole cationic lipid, and the DNA concentration in the DNA:lipid complexes is from about 1 mg/mL to about 2.5 mg/mL.

9. A method of introducing a recombinant expression construct into a cell within a tissue in an animal, the method comprising the step of administering the pharmaceutical composition of claim 1 to the animal by direct injection into the tissue in the animal, wherein the neutral lipid is cholesterol, the cationic lipid and the neutral lipid are present in a molar ratio of about 1:1 the complex of the recombinant expression construct and a mixture of a neutral lipid and a cationic lipid comprises a ratio of DNA to cationic lipid of about 1:1 µg DNA/nmole cationic lipid, and the DNA concentration in the DNA:lipid complexes is from about 1 mg/ml to about 2.5 mg/mL.

* * * * *

UNITED STATES PATENT AND TRADEMARK OFFICE
CERTIFICATE OF CORRECTION

PATENT NO.   : 5,830,878
DATED        : November 3, 1998
INVENTOR(S)  : Cori M. Gorman et al.

It is certified that error appears in the above-identified patent and that said Letters Patent is hereby corrected as shown below:

<u>Column 23,</u>
Lines 14-15, delete "1-(2-(oleoyloxy)ethyl)-2-oleoyloxy)ethyl)-2-oleyl-3-(2-hydroxyethyl)imidazolinium" and insert -- 1-(2-(oleoyloxy)ethyl)-2-oleyl-3-(2-hydroxyethyl)imidazolinium --.

Signed and Sealed this

Twenty-fourth Day of September, 2002

Attest:

JAMES E. ROGAN
Attesting Officer    Director of the United States Patent and Trademark Office